(12) United States Patent
Alterman et al.

(10) Patent No.: US 8,080,571 B2
(45) Date of Patent: Dec. 20, 2011

(54) TRICYCLIC ANGIOTENSIN II AGONISTS

(75) Inventors: Mathias Alterman, Stockholm (SE); Anders Hallberg, Uppsala (SE); Xiongyu Wu, Uppsala (SE)

(73) Assignee: Vicore Pharma AB, Gothenburg (SE)

(*) Notice: Subject to any disclaimer, the term of this patent is extended or adjusted under 35 U.S.C. 154(b) by 1050 days.

(21) Appl. No.: 11/918,240

(22) PCT Filed: Apr. 12, 2006

(86) PCT No.: PCT/GB2006/001319
§ 371 (c)(1), (2), (4) Date: Dec. 3, 2007

(87) PCT Pub. No.: WO2006/109048
PCT Pub. Date: Oct. 19, 2006

(65) Prior Publication Data
US 2009/0042931 A1 Feb. 12, 2009

Related U.S. Application Data

(60) Provisional application No. 60/670,251, filed on Apr. 12, 2005.

(51) Int. Cl.
| | |
|---|---|
| A61K 31/4155 | (2006.01) |
| A61K 31/4174 | (2006.01) |
| A61K 31/4178 | (2006.01) |
| A61K 31/4192 | (2006.01) |
| C07D 233/54 | (2006.01) |
| C07D 249/06 | (2006.01) |
| C07D 231/10 | (2006.01) |

(52) U.S. Cl. ...... 514/382; 548/250; 548/255; 548/262.2; 548/311.1; 548/364.1; 514/383; 514/385; 514/397

(58) Field of Classification Search .......... 548/250, 548/255, 262.2, 311.1, 364.1; 514/382, 383, 514/385, 397
See application file for complete search history.

(56) References Cited

U.S. PATENT DOCUMENTS

| | | | |
|---|---|---|---|
| 5,312,820 A | 5/1994 | Ashton et al. | |
| 5,424,450 A | 6/1995 | Boswell et al. | |
| 5,444,067 A | 8/1995 | Kivlighn et al. | |
| 5,512,681 A | 4/1996 | Boswell et al. | |
| 5,545,651 A | 8/1996 | Duncia et al. | |
| 6,335,451 B1 | 1/2002 | Kleemann et al. | |

FOREIGN PATENT DOCUMENTS

| | | |
|---|---|---|
| DE | 40 23 215 A1 | 1/1992 |
| EP | 0 399 731 A1 | 11/1990 |
| EP | 0 399 732 A1 | 11/1990 |
| EP | 0 499 415 A1 | 8/1992 |
| WO | WO 93/04045 | 3/1993 |
| WO | WO 93/04046 | 3/1993 |
| WO | WO 94/11379 A1 | 5/1994 |
| WO | WO 94/28896 | 12/1994 |
| WO | WO 99/43339 A1 | 9/1999 |
| WO | WO 02/096883 A1 | 12/2002 |
| WO | WO -02/096883 A1 * | 12/2002 |
| WO | WO 03/064414 A1 | 8/2003 |
| WO | WO 2004/046128 A1 | 6/2004 |
| WO | WO 2004/046137 A1 | 6/2004 |
| WO | WO 2004/046141 A1 | 6/2004 |
| WO | WO 2004/085420 A1 | 10/2004 |

OTHER PUBLICATIONS

Cramer, R.D., et al; "Prospective Identification of Biologically Active Structures by Topomer Shape Similarity Searching"; J. Med. Chem.; vol. 42; pp. 3919-3933 (1999).
Murugesan, N., et al; "Biphenylsulfonamide Endothelin Antagonists: Structure-Activity Relationships of a Series of Mono- and Disubstituted Analogues and Pharmacology of the Orally Active Endothelin Antagonist 2'-Amino-N-(3,4-dimethyl-5-isoxazolyl)-4'-(2-methylpropyl)[1,1'-biphenyl]-2-sulfonamide (BMS-187308)"; J. Med. Chem., vol. 41; pp. 5198-5218 (1998).
Smith, D.A., et al; "Pharmacokinetics and metabolism in Drug Design"; Wiley-VCH; pp. 3/7-4/7 (2001).
Wingstrand, J.; "An introduction to Medicinal Chemistry and Drug Discovery"; Lund University; pp. 5/7-7/7 (2005).
International Preliminary Report on Patentability; Int'l Appln. No. PCT/GB2006/001319; Int'l Filing Date Apr. 12, 2006 (6 pgs).
Ardaillou, R.; "Angiotensin II Receptors"; J. Am. Soc. Nephrol., 10: pp. 530-539 (1999).
De Gasparo, M., et al; "International Union of Pharmacology. XXIII. The Angiotensin II Receptors"; Pharmacol Rev.; 52, pp. 415-472 (2000).
Pandya, T., et al; "3-D QSAR Studies of Triazolinone Based Balanced $AT_1/AT_2$ Receptor Antagonists"; Bioorganic & Medicinal Chemistry; 9, pp. 291-300 (2001).

* cited by examiner

Primary Examiner — Joseph K. McKane
Assistant Examiner — Janet L Coppins
(74) Attorney, Agent, or Firm — Nixon & Vanderhye

(57) ABSTRACT

There is provided compounds of formula I,

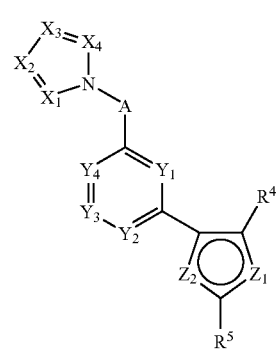

wherein A, $X_1$, $X_2$, $X_3$, $X_4$, $Y_1$, $Y_2$, $Y_3$, $Y_4$, $Z_1$, $Z_2$, $R^4$ and $R^5$ have meanings given in the description, and pharmaceutically-acceptable salts thereof, which compounds are useful as selective agonists of the AT2 receptor, and thus, in particular, in the treatment of inter alia gastrointestinal conditions, such as dyspepsia, IBS and MOF, and cardiovascular disorders.

20 Claims, No Drawings

TRICYCLIC ANGIOTENSIN II AGONISTS

This application is the U.S. National Phase of International Application PCT/GB2006/001319, filed 12 Apr. 2006, which designated the U.S. PCT/GB2006/001319 claims priority to U.S. Provisional Application No. 60/670,251 filed 12 Apr. 2005. The entire content of these applications are incorporated herein by reference.

FIELD OF THE INVENTION

This invention relates to novel pharmaceutically-useful compounds, in particular compounds that are angiotensin II (AngII) agonists, more particularly agonists of the AngII type 2 receptor (hereinafter the AT2 receptor), and especially agonists that bind selectively to that receptor. The invention further relates to the use of such compounds as medicaments, to pharmaceutical compositions containing them, and to synthetic routes to their production.

BACKGROUND AND PRIOR ART

The endogenous hormone AngII is a linear octapeptide ($Asp^1$-$Arg^2$-$Val^3$-$Tyr^4$-$Ile^5$-$His^6$-$Pro^7$-$Phe^8$), and is the active component of the renin-angiotensin system (RAS). It is produced by the sequential processing of the pro-hormone angiotensinogen by renin and angiotensin converting enzyme (ACE).

The renin-angiotensin system (RAS) plays an important role in the regulation of blood pressure, body fluid and electrolyte homeostasis. Ang II exerts these physiological actions in many organs including the kidneys, the adrenal glands, the heart, blood vessels, the brain, the gastrointestinal tract and the reproductive organs (de Gasparo et al, *Pharmacol. Rev.* (2000) 52, 415-472).

Two main classes of AngII receptors have been identified, and designated as the type 1 receptor (hereinafter the AT1 receptor) and the AT2 receptor. The AT1 receptor is expressed in most organs, and is believed to be responsible for the majority of the biological effects of AngII. The AT2 receptor is more prevalent than the AT1 receptor in fetal tissues, the adult ovaries, the adrenal medulla and the pancreas. An equal distribution is reported in the brain and uterus (Ardaillou, *J. Am. Soc. Nephrol.*, 10, S30-39 (1999)).

Several studies in adult individuals appear to demonstrate that, in the modulation of the response following AngII stimulation, activation of the AT2 receptor has opposing effects to those mediated by the AT1 receptor.

The AT2 receptor has also been shown to be involved in apoptosis and inhibition of cell proliferation (see de Gasparo et al, supra). Further, it seems to play a role in blood pressure control. For example, it has been shown in transgenic mice lacking AT2 receptors that their blood pressure was elevated. Furthermore, it has been concluded that the AT2 receptor is involved in exploratory behaviour, pain sensitivity and thermoregulation.

The expression of AT2 receptors has also been shown to increase during pathological circumstances, such as vascular injury, wound healing and heart failure (see de Gasparo et al, supra).

The expected pharmacological effects of agonism of the AT2 receptor are described generally in de Gasparo et al, supra.

More recently, AT2 receptor agonists have been shown to be of potential utility in the treatment and/or prophylaxis of disorders of the alimentary tract, such as dyspepsia and irritable bowel syndrome, as well as multiple organ failure (see international patent application WO 99/43339).

AngII antagonists (which bind to the AT1 and/or AT2 receptors) have been disclosed in inter alia international applications WO 93/04045, WO 93/04046, WO 94/11379 and WO 94/28896, U.S. Pat. Nos. 5,312,820 and 5,512,681, European patent applications EP 0 499 415, EP 399 731 and EP 399 732 and Pandya et al, *Bioorganic & Medicinal Chemistry*, 9, 291-300 (2001). The use of the compounds disclosed in these documents as agonists of AngII, and in particular the AT2 receptor, is not contemplated.

U.S. Pat. No. 5,444,067 discloses compounds comprising an imidazolyl group attached, via a methylene bridge, to a phenylthiophene moiety, as AngII agonists. The phenyl ring of the phenylthiophene moiety in these molecules is 1,4-disubstituted with the thiophene and the imidazolyl group (which is attached via a methylene bridge).

More recently, international patent applications WO 02/96883, WO 03/064414, WO 2004/085420, WO 2004/046128, WO 2004/046141 and WO 2004/046137 have disclosed various multicyclic compounds as agonists of AngII and in particular as selective AT2 receptor agonists. In the compounds disclosed in these documents, a central aryl ring is disubstituted in the 1,4 (sara) configuration. None of these documents mention or suggest compounds in which such an aryl group is disubstituted in the 1,3 (meta) configuration.

We have now found that such compounds are effective and/or selective AT2 receptor agonists and are therefore expected to find utility in inter alia the above-mentioned conditions.

DISCLOSURE OF THE INVENTION

According to the invention there is provided a compound of formula I,

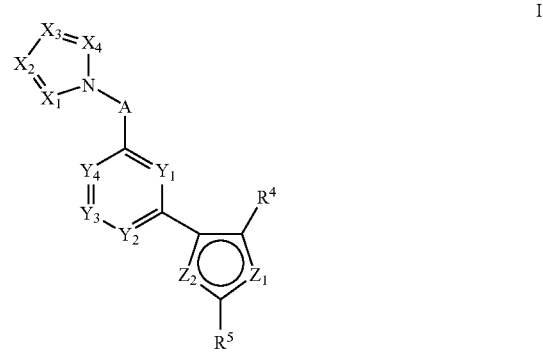

wherein
A represents —$CH_2$—, —C(O)—, —C(O)—$CH_2$— (in which the —C(O)— group is attached to the ring bearing $Y_1$, $Y_2$, $Y_3$ and $Y_4$) or —$CH_2$—$CH_2$—;
one of $X_1$ and $X_2$ represents —N— and the other represents —C($R^1$)—;
$X_3$ represents —N— or —C($R^2$)—;
$X_4$ represents —N— or —C($R^3$)—;
$R^1$, $R^2$ and $R^3$ independently represent H, $C_{1-6}$ alkyl, $C_{1-6}$ alkoxy, $C_{1-6}$ alkoxy-$C_{1-6}$-alkyl, $Ar^1$, $Het^1$, $C_{1-3}$ alkyl-$Ar^2$, $C_{1-3}$ alkyl-$Het^2$, $C_{1-3}$ alkoxy-$Ar^3$, $C_{1-3}$ alkoxy-$Het^3$, halo, —C(O)—$C_{1-6}$ alkyl, —C(O)—$Ar^4$ or —C(O)—$Het^4$; or
$R^2$ and $R^3$ may be linked to form, along with the carbon atoms to which they are attached, a 5- or 6-membered aromatic ring optionally containing one to three heteroatoms;

$Ar^1$, $Ar^2$, $Ar^3$ and $Ar^4$ each independently represent a $C_{6-10}$ aryl group, which group is optionally substituted by one or more substituents selected from =O, —OH, cyano, halo, nitro, $C_{1-6}$ alkyl (optionally terminated by —N(H)C(O)OR$^{11a}$), $C_{1-6}$ alkoxy, phenyl, —N(R$^{12a}$)R$^{12b}$, —C(O)R$^{12c}$, —C(O)OR$^{12d}$, —C(O)N(R$^{12e}$)R$^{12f}$, —N(R$^{12g}$)C(O)R$^{12h}$, —N(R$^{12i}$)C(O)N(R$^{12j}$)R$^{12k}$, —N(R$^{12m}$)S(O)$_2$R$^{11b}$, —S(O)$_n$R$^{11c}$, —OS(O)$_2$R$^{11d}$ and —S(O)$_2$N(R$^{12n}$)R$^{12p}$;

Het$^1$, Het$^2$, Het$^3$ and Het$^4$ each independently represent a four- to twelve-membered heterocyclic group containing one or more heteroatoms selected from oxygen, nitrogen and/or sulfur, which heterocyclic group is optionally substituted by one or more substituents selected from =O, —OH, cyano, halo, nitro, $C_{1-6}$ alkyl (optionally terminated by —N(H)C(O)OR$^{11a}$), $C_{1-6}$ alkoxy, phenyl, —N(R$^{12a}$)R$^{12b}$, —C(O)R$^{12c}$, —C(O)OR$^{12d}$, —C(O)N(R$^{12e}$)R$^{12f}$, —N(R$^{12g}$)C(O)R$^{12h}$, —N(R$^{12i}$)C(O)N(R$^{12j}$)R$^{12k}$, —N(R$^{12m}$)S(O)$_2$R$^{11b}$, —S(O)$_n$R$^{11c}$, —OS(O)$_2$R$^{11d}$ and —S(O)$_2$N(R$^{12n}$)R$^{12p}$;

$R^{11a}$ to $R^{11d}$ independently represent, on each occasion when used herein, $C_{1-6}$ alkyl;

$R^{12a}$ to $R^{12p}$ independently represent, on each occasion when used herein, H or $C_{1-6}$ alkyl;

n represents 0, 1 or 2;

$Y_1$, $Y_2$, $Y_3$ and $Y_4$ independently represent —CH— or —CF—;

$Z_1$ represents —CH—, —O—, —S—, —N— or —CH=CH—;

$Z_2$ represents —CH—, —O—, —S— or —N—;

provided that:
(a) $Z_1$ and $Z_2$ are not the same;
(b) when $Z_1$ represents —CH=CH—, then $Z_2$ may only represent —CH— or —N—; and
(c) other than in the specific case in which $Z_1$ represents —CH=CH—, and $Z_2$ represents —CH—, when one $Z_1$ and $Z_2$ represents —CH—, then the other represents —O— or —S—;

$R^4$ represents —S(O)$_2$N(H)C(O)R$^6$, —S(O)$_2$N(H)S(O)$_2$R$^6$, —C(O)N(H)S(O)$_2$R$^6$, or, when $Z_1$ represents —CH=CH—, R$^4$ may represent —N(H)S(O)$_2$N(H)C(O)R$^7$ or —N(H)C(O)N(H)S(O)$_2$R$^7$;

$R^5$ represents $C_{1-6}$ alkyl, $C_{1-6}$ alkoxy, $C_{1-6}$ alkoxy-$C_{1-6}$-alkyl or di-$C_{1-3}$-alkylamino-$C_{1-4}$-alkyl;

$R^6$ represents $C_{1-6}$ alkyl, $C_{1-6}$ alkoxy, $C_{1-6}$ alkoxy-$C_{1-6}$-alkyl, $C_{1-3}$ alkoxy-$C_{1-6}$-alkoxy, $C_{1-6}$ alkylamino or di-$C_{1-6}$ alkylamino; and $R^7$ represents $C_{1-6}$ alkyl, or a pharmaceutically-acceptable salt thereof,
which compounds and salts are referred to together hereinafter as "the compounds of the invention".

Pharmaceutically-acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo or by freeze-drying). Salts may also be prepared by exchanging a counter-ion of a compound of the invention in the form of a salt with another counter-ion, for example using a suitable ion exchange resin.

Unless otherwise specified, alkyl groups, and the alkyl parts of alkoxy, alkoxyalkyl, alkoxyalkoxy, alkylamino, alkylaminoalkyl groups, alkyl-aryl, alkyl-heterocyclic groups, alkoxy-aryl and alkoxy-heterocyclic groups, as defined herein may be straight-chain or, when there is a sufficient number (i.e. a minimum of three) of carbon atoms, be branched-chain, and/or cyclic. Further, when there is a sufficient number (i.e. a minimum of four) of carbon atoms, such groups may also be part cyclic. Such alkyl groups, and alkyl parts of alkoxy, alkoxyalkyl, alkoxyalkoxy, alkylamino, alkylaminoalkyl, alkyl-aryl, alkyl-heterocyclic, alkoxy-aryl and alkoxy-heterocyclic groups, may also be saturated or, when there is a sufficient number (i.e. a minimum of two) of carbon atoms, be unsaturated. Unless otherwise specified, such groups may also be substituted by one or more halo, and especially fluoro, atoms.

For the avoidance of doubt, alkoxy and alkoxyalkoxy groups are attached to the rest of the molecule via the/an oxygen atom in that group, alkylamino groups are attached to the rest of the molecule via the nitrogen atom of the amino part of that group, alkylaminoalkyl, alkoxyalkyl alkyl-aryl and alkyl-heterocyclic groups are attached to the rest of the molecule via the alkyl part of that group and alkoxy-aryl and alkoxy-heterocyclic groups are attached to the rest of the molecule via the alkyl part of the alkoxy part of that group.

The term "halo", when used herein, includes fluoro, chloro, bromo and iodo.

For the avoidance of doubt, in cases in which the identity of two or more substituents in a compound of the invention (for example $R^1$ and $R^2$) may be the same, the actual identities of the respective substituents are not in any way interdependent. For example, in the situation in which $R^1$ and $R^2$ both represent $C_{1-6}$ alkyl groups, the two alkyl groups in question may be the same or different. Similarly, when aryl and heterocyclic groups are substituted by more than one substituent as defined herein, the identities of the individual substituents are not to be regarded as being interdependent.

$C_{6-10}$ aryl groups include phenyl, naphthyl and the like (preferably phenyl). Preferred optional substituents on aromatic groups include halo, —OH, cyano, nitro, $C_{1-6}$ (e.g. $C_{1-3}$) alkyl groups (such as methyl) and $C_{1-6}$ (e.g. $C_{1-3}$) alkoxy groups.

Het (Het$^1$, Het$^2$, Het$^3$ and Het$^4$) groups that may be mentioned include those containing 1 to 4 heteroatoms (selected from the group oxygen, nitrogen and/or sulfur) and in which the total number of atoms in the ring system are between five and twelve. Het (Het$^1$, Het$^2$, Het$^3$ and Het$^4$) groups may be fully saturated, wholly aromatic, partly aromatic and/or bicyclic in character. Heterocyclic groups that may be mentioned include benzodioxanyl, benzodioxepanyl, benzodioxolyl, benzofuranyl, benzofurazanyl, benzimidazolyl, benzomorpholinyl, benzothiophenyl, chromanyl, cinnolinyl, dioxanyl, furanyl, hydantoinyl, imidazolyl, imidazo[1,2-a]pyridinyl, indolyl, isoquinolinyl, isoxazolyl, maleimido, morpholinyl, oxazolyl, phthalazinyl, piperazinyl, piperidinyl, purinyl, pyranyl, pyrazinyl, pyrazolyl, pyridinyl, pyrimindinyl, pyrrolidinonyl, pyrrolidinyl, pyrrolinyl, pyrrolyl, quinazolinyl, quinolinyl, 3-sulfolenyl, tetrahydropyranyl, tetrahydrofuranyl, thiazolyl, thiophenyl, thiochromanyl, triazolyl, tetrazolyl and the like. Values of Het$^1$ that may be mentioned include furanyl, thiazolyl and, more particularly, thiophenyl (e.g. 2-thiophenyl or 3-thiophenyl) and pyridinyl (e.g. 2-pyridinyl). Values of Het$^2$ that may be mentioned include furanyl, thiophenyl, thiazolyl and pyridinyl. Values of Het$^3$ and Het$^4$ that may be mentioned include pyridinyl.

Substituents on Het (Het$^1$, Het$^2$, Het$^3$ and Het$^4$) groups may, where appropriate, be located on any atom in the ring system including a heteroatom. The point of attachment of Het (Het$^1$, Het$^2$, Het$^3$ and Het$^4$) groups may be via any atom in the ring system including (where appropriate) a heteroatom, or an atom on any fused carbocyclic ring that may be present as part of the ring system. Het (Het$^1$, Het$^2$, Het$^3$ and Het$^4$) groups may also be in the N- or S-oxidised form.

Preferred ring systems comprising the substituents $Y_1$, $Y_2$, $Y_3$ and $Y_4$ include phenyl groups. For the avoidance of doubt, the ring systems in compounds of formula I that comprise the groups $Z_1$ and $Z_2$, are aromatic in nature. In some instances, for example in cases where one of $Z_1$ and $Z_2$ represents —N—, the skilled person will appreciate that an additional H atom may necessarily be bonded to that N atom, in order to ensure that the rules of valency are adhered to. Preferred ring systems comprising $Z_1$ and $Z_2$ include oxazole groups, thiazole groups, pyridinyl groups, furanyl groups and, more particularly, thiophenyl groups and phenyl groups.

In this respect, compounds of the invention may exhibit tautomerism. All tautomeric forms and mixtures thereof are included within the scope of the invention.

Compounds of the invention also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

Preferred compounds of the invention include those in which:
  (i) when $X_1$ represents —C($R^1$)—, then:
    (a) $X_3$ represents —C($R^2$)— and $X_4$ represents —N—;
    (b) $X_3$ and $X_4$ both represent N; or, more preferably,
    (c) $X_3$ represents —C($R^2$)— and $X_4$ represents —C($R^3$)—; or
  (ii) when $X_1$ represents —N—, then
    (a) $X_3$ represents —N— and $X_4$ represents —C($R^3$)—;
    (b) $X_3$ and $X_4$ both represent —N—; or, more preferably,
    (c) $X_3$ represents —C($R^2$) and $X_4$ represents —C($R^3$)—.

Preferred compounds of formula I include those in which:
A represents —$CH_2$—, —C(O)—$CH_2$— or —$CH_2$—$CH_2$—;
$X_3$ represents —C($R^2$)—;
$X_4$ represents —C($R^3$)—;
$R^1$ represents:
hydrogen; halo (e.g. chloro);
$C_{1-4}$ alkyl, such as methyl, ethyl and butyl (e.g. n-butyl), which alkyl group is optionally substituted by one or more fluoro atoms (so forming, for example, a trifluoromethyl group);
$Ar^1$, such as phenyl;
$Het^1$, such as thiophenyl (e.g. 2-thiophenyl or 3-thiophenyl) or pyridinyl (e.g. 2-pyridinyl); or
—C(O)—$C_{1-3}$ alkyl (e.g. —C(O)-methyl);
$R^2$ represents $C_{1-3}$ alkyl, or, especially, H;
$R^3$ represents $C_{1-3}$ alkyl, or, especially, H; or
$R^2$ and $R^3$ are linked to form a further benzene ring, optionally containing one or two (e.g. one) heteroatoms (e.g. nitrogen), so forming, for example, a pyridine ring;
$Y_1$, $Y_2$, $Y_3$ and $Y_4$ all represent —CH—;
$Z_1$ represents —CH═CH— or, especially, —S—;
$Z_2$ represents —CH—;
$R^4$ represents —S(O)$_2$N(H)C(O)$R^6$;
$R^5$ represents $C_{1-4}$ alkyl such as n-butyl or, more particularly, isobutyl;
$R^6$ represents $C_{1-4}$ alkoxy-$C_{1-3}$ alkyl or $C_{1-4}$ alkoxy (such as n-butoxymethyl, iso-butoxy and especially, n-butoxy).

Preferred ring systems comprising the substituents $X_1$, $X_2$, $X_3$ and $X_4$ include 1,2,4-triazole groups, tetrazole groups and, more particularly, pyrazole groups and imidazole groups.

When $R^4$ represents —S(O)$_2$N(H)C(O)$R^6$, —S(O)$_2$N(H)S(O)$_2R^6$ or —C(O)N(H)S(O)$_2R^6$, preferred values of $R^6$ include n-butoxymethyl, iso-butoxy and especially, n-butoxy.

When $X_3$ and $X_4$ represent —C($R^2$)— and —C($R^3$)—, respectively, and $R^2$ and $R^3$ are linked, then it is preferred that: $X^1$ represents —C($R^1$)— and $X^2$ represents —N—; and/or the resultant biaryl ring system represents a 5,6-fused biaryl ring system, such as a benzoimidazolyl (e.g. benzoimidazol-1-yl) group or an azobenzoimidazolyl (e.g. imidazo[4,5-b]pyridine-3-yl or imidazo[4,5-b]pyridine-1-yl) group.

More preferred compounds of the invention include the compounds of the examples described hereinafter.

Compounds of formula I may be made in accordance with techniques well known to those skilled in the art, for example as described hereinafter.

According to a further aspect of the invention there is provided a process for the preparation of a compound of formula I, which process comprises:
(i) for compounds of formula I in which $R^4$ represents —S(O)$_2$N(H)C(O)$R^6$ or —S(O)$_2$N(H)S(O)$_2R^6$, and $R^6$ is as hereinbefore defined, reaction of a compound of formula II,

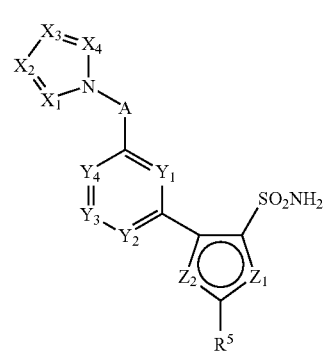

II wherein A, $X_1$, $X_2$, $X_3$, $X_4$, $Y_1$, $Y_2$, $Y_3$, $Y_4$, $Z_1$, $Z_2$ and $R^5$ are as hereinbefore defined with a compound of formula III, $R^6GL^1$   III wherein G represents —C(O)— or —S(O)$_2$— (as appropriate), $L^1$ represents a suitable leaving group, such as halo (e.g. chloro or bromo) and $R^6$ is as hereinbefore defined, for example at around room temperature or above (e.g. up to 60-70° C.) in the presence of a suitable base (e.g. pyrrolidinopyridine, pyridine, triethylamine, tributylamine, trimethylamine, dimethylaminopyridine, di-iso-propylamine, 1,8-diazabicyclo[5.4.0]undec-7-ene, sodium hydroxide, sodium carbonate, or mixtures thereof) and an appropriate solvent (e.g. pyridine, dichloromethane, chloroform, tetrahydrofuran, dimethylformamide, trifluoromethylbenzene, triethylamine, water, or mixtures thereof). Preferred base/solvent systems for compounds of formula III in which G is —C(O)— include pyrrolidinopyridine/pyridine, pyrrolidinopyridine/triethylamine, dimethylaminopyridine/pyridine, dimethylaminopyridine/triethylamine, sodium carbonate/dichloromethane/water or pyrrolidinopyridine/triethylamine/dichloromethane. Preferred base/solvent systems for compounds of formula III in which G is —S(O)$_2$— include NaOH/THF;
(ii) for compounds of formula I in which $R^4$ represents —S(O)$_2$N(H)C(O)$R^6$ and $R^6$ represents $C_{1-6}$ alkoxy-$C_{1-6}$- alkyl, coupling of a compound of formula II as hereinbefore defined with a compound of formula IV,

wherein $R^{6a}$ represents $C_{1-6}$ alkoxy-$C_{1-6}$-alkyl, for example under similar conditions to those described under process step (i) above, in the presence of a suitable coupling reagent (e.g. 1,1'-carbonyl-diimidazole, N,N'-dicyclohexylcarbodiimide, N,N'-disuccinimidyl carbonate, benzotriazole-1-yloxytris(dimethylamino)phosphoniumhexafluorophosphate, 2-(1H-benzotriazole-1-yl)-1,1,3,3-tetramethyluronium hexafluorophosphate, benzotriazole-1-yl-oxy-tris-pyrrolidino-phosphonium hexafluorophosphate, bromo-tris-pyrrolidinophosphonium hexafluorophosphate or 2-(1H-benzotriazole-1-yl)-1,1,3,3-tetramethyluronium tetrafluorocarbonate), a suitable base (as mentioned in process step (i) above) and an appropriate solvent (as mentioned in process step (i) above);

(iii) for compounds of formula I in which $R^4$ represents —C(O)N(H)S(O)$_2$R$^6$ and R$^6$ is as hereinbefore defined, coupling of a compound of formula V,

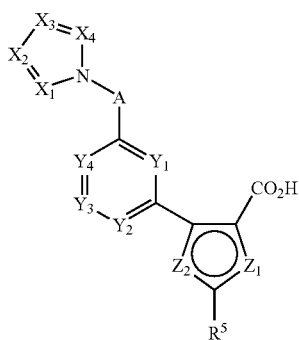

wherein A, $X_1$, $X_2$, $X_3$, $X_4$, $Y_1$, $Y_2$, $Y_3$, $Y_4$, $Z_1$, $Z_2$ and $R^5$ are as hereinbefore defined with a compound of formula VI,

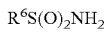

wherein $R^6$ is as hereinbefore defined, for example in the presence of a suitable coupling reagent (such as those described in process step (ii) hereinbefore), and under similar reaction conditions to those described hereinbefore for preparation of compounds of formula I in which $R^4$ represents —S(O)$_2$N(H)C(O)R$^6$ and R$^6$ represents $C_{1-6}$ alkoxy-$C_{1-6}$-alkyl (i.e. process step (ii));

(iv) for compounds of formula I in which $R^4$ represents —C(O)N(H)S(O)$_2$R$^6$ and R$^6$ is as hereinbefore defined, coupling of a compound of formula VII,

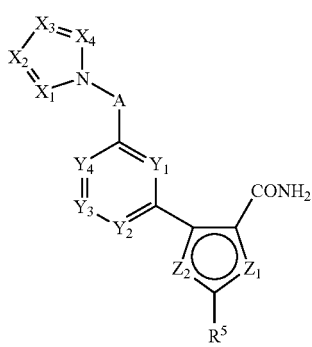

wherein A, $X_1$, $X_2$, $X_3$, $X_4$, $Y_1$, $Y_2$, $Y_3$, $Y_4$, $Z_1$, $Z_2$ and $R^5$ are as hereinbefore defined with a compound of formula VIII,

wherein $R^6$ is as hereinbefore defined, for example at around 50° C. in the presence of a suitable base (e.g. sodium hydride) and an appropriate organic solvent (e.g. THF);

(v) for compounds of formula I in which $R^4$ represents —N(H)S(O)$_2$N(H)C(O)R$^7$ and R$^7$ is as hereinbefore defined, reaction of a compound of formula IX,

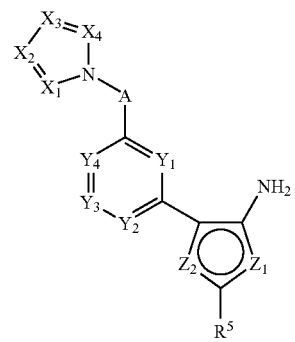

wherein A, $X_1$, $X_2$, $X_3$, $X_4$, $Y_1$, $Y_2$, $Y_3$, $Y_4$, $Z_1$, $Z_2$ and $R^5$ are as hereinbefore defined with a compound of formula X,

wherein $R^7$ is as hereinbefore defined, for example at or around room temperature in the presence of a suitable base (e.g. sodium hydroxide or triethylamine) and a suitable organic solvent (e.g. benzene or dichloromethane);

(vi) for compounds of formula I in which $R^4$ represents —N(H)C(O)N(H)S(O)$_2$R$^7$ and R$^7$ is as hereinbefore defined, reaction of a compound of formula IX as hereinbefore defined with a compound of formula XI,

wherein $R^x$ represents a suitable leaving group, such as a halo (e.g. chloro or bromo) group or alkoxy (e.g. —O—$C_{1-2}$ alkyl) and $R^7$ is as hereinbefore defined, for example at or around room temperature in the presence of a suitable organic solvent (e.g. dichloromethane). Alternatively Rx may represent —OH, in which case the coupling reaction may be performed under conditions such as those hereinbefore described in respect of process (ii) above;

(vii) for compounds of formula I in which $R^4$ represents —N(H)C(O)N(H)S(O)$_2$R$^7$ and R$^7$ is as hereinbefore defined, reaction of a compound of formula IX as hereinbefore defined with an isocyanate compound of formula XII,

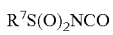

wherein $R^7$ is as hereinbefore defined, for example at or around room temperature in the presence of a suitable organic solvent (e.g. dichloromethane);

(viii) for compounds of formula I in which $R^4$ represents —S(O)$_2$N(H)C(O)R$^6$ and R$^6$ represents $C_{1-6}$ alkylamino, reaction of a compound of formula II as hereinbefore defined with an isocyanate compound of formula XII,

wherein $R^{6b}$ is $C_{1-6}$ alkyl, for example at or around room temperature in the presence of a suitable base (e.g. sodium hydroxide or potassium hydroxide and an appropriate organic solvent (e.g. acetone or acetonitrile);

(ix) for compounds of formula I in which $R^4$ represents —S(O)$_2$N(H)C(O)R$^6$ and $R^6$ represents di-C$_{1-6}$ alkylamino, reaction of a corresponding compound of formula I in which $R^4$ represents —S(O)$_2$N(H)C(O)R$^6$ and $R^6$ represents C$_{1-6}$ alkoxy with an amine of formula XIV,

XIV wherein $R^{6c}$ and $R^{6d}$ independently represent C$_{1-6}$ alkyl, for example at above room temperature (e.g. at between 70° C. and 100° C.) in the presence of an appropriate organic solvent (e.g. toluene); or (x) for compounds of formula I in which $R^1$, $R^2$ or $R^3$ represent halo, reaction of a compound corresponding to a compound of formula I in which $R^1$, $R^2$ and/or $R^3$ represents an appropriate leaving group (such as a pyridinium group) with a source of halide (e.g. chloride, bromide or iodide) ions under reaction conditions known to those skilled in the art.

Compounds of formula II may be prepared by reaction of a compound of formula XV,

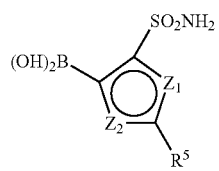

XV wherein $R^5$, $Z^1$ and $Z^2$ are as hereinbefore defined, or a N-protected derivative thereof, with a compound of formula XVI,

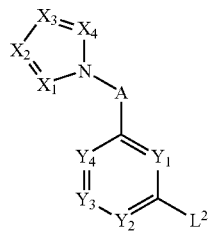

XVI wherein $L^2$ represents a suitable leaving group, such as such as methylsulphonate (e.g. trifluoromethylsulphonate), or halo, such as iodo or bromo, and A, $X_1$, $X_2$, $X_3$, $X_4$, $Y_1$, $Y_2$, $Y_3$ and $Y_4$ are as hereinbefore defined, for example in the presence of an appropriate coupling catalyst system (e.g. a palladium catalyst, such as Pd(PPh$_3$)$_4$ or Pd(OAc)$_2$/ligand (wherein the ligand may be, for example, PPh$_3$, P(o-Tol)$_3$ or 1,1'-bis(diphenylphosphino)ferrocene)) and a suitable base (e.g. sodium hydroxide, sodium carbonate, potassium carbonate, cesium carbonate, triethylamine or di-iso-propylamine)), as well as a suitable solvent system (e.g. toluene, ethanol, dimethoxymethane, dimethylformamide, ethylene glycol dimethyl ether, water, dioxane or mixtures thereof). This reaction may be carried out at above room temperature (e.g. at the reflux temperature of the solvent system that is employed). If a protected version of a compound of formula XV is employed, this reaction may be followed by deprotection of the SO$_2$NH-group under standard conditions, for example as described hereinafter.

Compounds of formula II in which $R^1$, $R^2$ and $R^3$ do not represent H or halo, may be prepared by reaction of a corresponding compound of formula II in which $R^1$, $R^2$ and/or $R^3$ (as appropriate) represents halo (e.g. bromo) with a compound of formula XVIa,

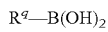

XVIa wherein $R^q$ represents $R^1$, $R^2$ or $R^3$ (as appropriate), provided that it does not represent H or halo, for example under similar conditions to those described above in respect of the first process for the preparation of compounds of formula II.

Compounds of formula II may alternatively be prepared by reaction of a compound of formula XVII,

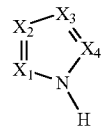

XVII wherein $X_1$, $X_2$, $X_3$ and $X_4$ are as hereinbefore defined with a compound of formula XVIII,

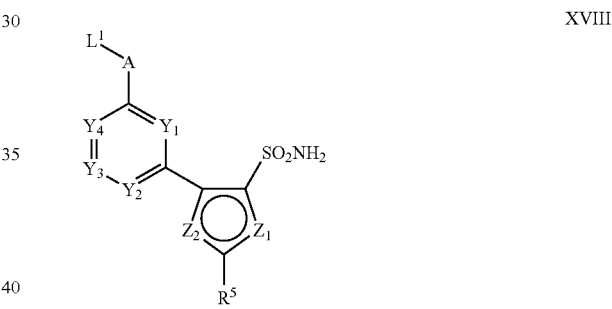

XVIII wherein A, $Y_1$, $Y_2$, $Y_3$, $Y_4$, $Z_1$, $Z_2$, $R^5$ and $L^1$ are as hereinbefore defined ($L^1$, in particular, may represent bromo), or a N-protected derivative thereof, for example at around, below or, preferably, above room temperature (e.g. at 80° C.), optionally in the presence of a suitable base (e.g. potassium tert-butoxide, potassium hydroxide, sodium hydroxide, sodium carbonate, triethylamine or di-iso-propylethylamine) and an appropriate organic solvent (e.g. DMSO, dioxane, DMF, THF or CH$_2$Cl$_2$). In the case where base is not employed, the skilled person will appreciate that at least two equivalents of the compound of formula XVII may need to be employed. If a protected version of a compound of formula XVIII is employed, this reaction may be followed by deprotection of the SO$_2$NH-group under standard conditions, for example as described hereinafter. Additionally, compounds of formula II in which $Z_1$ is —CH=CH— and $Z_2$ is —CH— may be prepared by analogy with the processes described in inter alia U.S. Pat. No. 5,312,820. Further, compounds of formula II in which $Z_1$ is —S— and $Z_2$ is —CH— may be prepared by analogy with processes described in inter alia UK patent application GB 2281298.

Compounds of formula V may be prepared by oxidation of a compound of formula XIX,

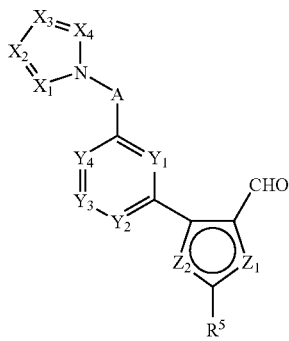

XIX wherein A, $X_1$, $X_2$, $X_3$, $X_4$, $Y_1$, $Y_2$, $Y_3$, $Y_4$, $Z_1$, $Z_2$ and $R^5$ are as hereinbefore defined, for example under standard oxidation conditions in the presence of a suitable oxidising agent, such as potassium permanganate or chromium (VI) oxide.

Compounds of formulae VII and IX may be prepared by reaction of a compound of formula XVI as hereinbefore defined with (in the case of a compound of formula VII) a compound of formula XX,

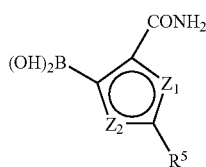

XX or (in the case of a compound of formula IX) a compound of formula XXI,

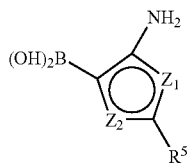

XXI wherein, in both cases, $Z_1$, $Z_2$ and $R^5$ are as hereinbefore defined, or N-protected derivatives thereof, for example under similar conditions to those described hereinbefore for preparation of compounds of formula II (first process). If protected versions of compounds of formulae XX and XXI are employed, these reactions may be followed by deprotection of the NH-group under standard conditions (e.g. employing acid).

Compounds of formula XVI may be prepared by standard techniques, for example by way of reaction of a compound of formula XVII as hereinbefore defined with a compound of formula XXII,

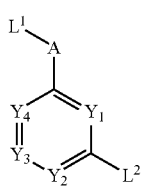

XXII wherein A, $Y_1$, $Y_2$, $Y_3$, $Y_4$, $L^1$ and $L^2$ are as hereinbefore defined, for example under similar conditions to those described hereinbefore in respect of preparation of compounds of formula II (third process).

Compounds of formula XVI in which A represents —$CH_2$— or —$CH_2$—$CH_2$— may be prepared by reduction of a corresponding compound of formula XVI in which A represents —C(O)— or —C(O)—$CH_2$, respectively. In each case suitable reducing conditions (e.g. using a chemoselective reducing agent) may be employed. In the former case, appropriate reducing agents include borane and lithium aluminium hydride. In the latter case, suitable conditions include: employing $NaBH_4$ in the presence of an acid (e.g. $CH_3COOH$ or $CF_3COOH$); Wolff-Kishner reduction conditions (i.e. by conversion of the carbonyl group to a hydrazone, followed by base induced elimination); conversion of the carbonyl to the thioacetal analogue (e.g. by reaction with a dithiane) followed by reduction with e.g. Raney nickel; reduction to the corresponding alcohol (e.g. in the presence of $NaBH_4$ in an alcoholic solvent), followed by conversion of the alcohol to the corresponding thioester (e.g. by employing $CS_2$ in base and a solvent (e.g. NaH in THF), reaction with an alkyl halide for conversion to the corresponding alkyl thioester) and finally by treating the alkyl thioester so formed with an appropriate reagent or mixture of reagents, such as ($C_{1-6}$ alkyl)$_3$SnH (e.g. (Butyl)$_3$SnH) and a catalytic amount of AIBN (azo-iso-butyronitrile), di-alkyl (e.g. di-$C_{1-6}$ alkyl) phosphites or hypophosphorous acid, all under reaction conditions known to those skilled in the art (for example in the case of reaction with ($C_{1-6}$ alkyl)$_3$SnH and AIBN, in the presence of a suitable solvent (e.g. THF) at elevated temperature (e.g. reflux)), or reduction in the presence of hypophosphorous acid with iodine in acetic acid.

Compounds of formula XVII are readily available. For example, compounds of formula XVII in which $X^1$ and/or $X^4$ represent —C($R^1$)— and —C($R^3$)—, respectively, and $R^1$ and/or $R^3$ represent $C_{1-6}$ alkyl, $C_{1-6}$ alkoxy-$C_{1-6}$ alkyl, $C_{1-3}$ alkyl-$A^2$, $C_{1-3}$ alkyl-Het$^2$, halo, —C(O)—$C_{1-6}$ alkyl, —C(O)—Ar$^4$ or —C(O)—Het$^4$, may be prepared in accordance with literature procedures described hereinafter or by reaction of a corresponding compound of formula I in which $R^1$ and/or $R^3$ (as appropriate) represent hydrogen with a suitable base (such as a lithium metal base (e.g. BuLi and especially, n-BuLi) followed by quenching with a compound of formula XXIIa, $R^{q2}L^1$            XXIIa wherein $R^{q2}$ represents $C_{1-6}$ alkyl, $C_{1-6}$ alkoxy-$C_{1-6}$ alkyl, $C_{1-3}$ alkyl-Ar$^2$, $C_{1-3}$ alkyl-Het$^2$, halo, —C(O)—$C_{1-6}$ alkyl, —C(O)—Ar$^4$ or —C(O)—Het$^4$ and $L^1$ is as hereinbefore defined. This reaction may be performed in the presence of an appropriate solvent, such as a polar aprotic solvent (e.g. THF) at, for example below room temperature (e.g. between 0° C. and −78° C.), followed by the addition of an appropriate compound of formula XXIIa (e.g. an alkyl bromide for the introduction of a $C_{1-6}$ alkyl group or $CH_3CON(CH_3)_2$ for the introduction of a —C(O)—$CH_3$ group). The skilled person will appreciate that the NH group of the compound of formula XVII may first need to be protected (e.g. by a diethoxymethyl group, which may be introduced by reaction of HC(OEt)$_3$ and acid (e.g. p-toluenesulfonic acid)) and subsequently removed (e.g. by acid hydrolysis). Compounds of formula XVIII may be prepared by analogy with the processes described in inter alia U.S. Pat. No. 5,312,820, UK patent application GB 2281298, and/or by reaction of a compound of formula XV as hereinbefore defined with a compound of formula XXIII,

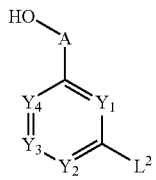

XXIII wherein A, $Y_1$, $Y_2$, $Y_3$, $Y_4$ and $L^2$ are as hereinbefore defined, for example under similar conditions to those described hereinbefore in respect of preparation of compounds of formula II (first process), followed by conversion of the OH group in the resultant intermediate to an appropriate leaving group, $L^1$ (e.g., in the case where $L^1$ is bromo, conversion may be carried out by reaction with $CBr_4$, for example at or around room temperature in the presence of a base (e.g. triphenylphosphine) and a suitable organic solvent (e.g. DMF)). Alternatively, the hydroxyl group may be converted to a sulfonate leaving group (e.g. mesylate or triflate) by employing a suitable reagent (e.g. a sulfonyl halide such as tosyl chloride, mesyl chloride or triflic anhydride).

Compounds of formula XIX may be prepared by reaction of a compound of formula XVI as hereinbefore defined with a compound of formula XXIV,

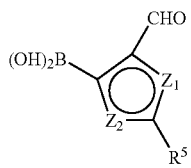

XXIV wherein $Z_1$, $Z_2$ and $R^5$ are as hereinbefore defined, or a protected (at the aldehyde part) derivative thereof, for example under similar conditions to those described hereinbefore for preparation of compounds of formula II (first process). If a protected version of a compound of formula XXIV is employed, this reaction may be followed by deprotection of the CHO-group under standard conditions (e.g. acid hydrolysis).

Compounds of formulae XV, XX, XXI and XXIV and protected derivatives thereof may be prepared by reaction of a corresponding compound of formula XXV,

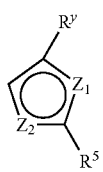

XXV wherein $R^y$ represents —$S(O)_2NH_2$, —$C(O)NH_2$, —$NH_2$ or —CHO (as appropriate) and $R^5$, $Z_1$ and $Z_2$ are as hereinbefore defined, or an appropriate protected derivative thereof, with a reagent system that will enable the introduction of the —$B(OH)_2$ into the appropriate ring system. Suitable reagent systems include trialkylborates (e.g. tri-iso-propylborate). Such reactions may be carried out, for example, at low temperature (e.g. between −100° C. and 0° C., e.g. between −80° C. (such as −78° C.) and −10° C. (such as −20° C.)) in the presence of a suitable base (e.g. n-butyl lithium) and an appropriate organic solvent (e.g. THF), followed by acid hydrolysis (e.g. in the presence of dilute HCl).

Compounds of formula XXV are available using known techniques. For example:

(a) Compounds of formula XXV in which $R^y$ represents —$S(O)_2NH_2$, —$C(O)NH_2$ or —CHO, and protected derivatives thereof, may be prepared by reaction of a compound of formula XXVI,

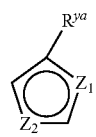

XXVI wherein $R^{ya}$ represents —$S(O)_2NH_2$, —$C(O)NH_2$ or —CHO and $Z_1$ and $Z_2$ are as hereinbefore defined, or a protected derivative thereof, with a compound of formula XXVII, $R^5L^3$      XXVII wherein $L^3$ represents a suitable leaving group (such as toluenesulphonate, benzenesulphonate, methanesulphonate or halo, such as bromo or iodo) and $R^5$ is as hereinbefore defined, for example at below room temperature (e.g. between around −35° C. and around −85° C.), in the presence of a suitable base (e.g. n-butyl lithium) and an appropriate solvent (e.g. THF).

(b) Compounds of formula XXV in which $R^y$ is —$S(O)_2NH_2$ and N-protected derivatives thereof, may be prepared by reaction of an appropriate compound of formula XXVIII,

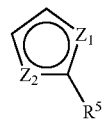

XXVIII wherein $R^5$, $Z_1$ and $Z_2$ are as hereinbefore defined with an appropriate reagent for introduction of a —$S(O)_2NH_2$ group into the appropriate ring system (for example chlorosulphonic acid, or thionyl chloride in the presence of a suitable strong base (e.g. butyl lithium)), followed by reaction of the resultant intermediate with ammonia, or a protected derivative thereof (e.g. tert-butylamine), under conditions that are well known to those skilled in the art.

(c) Certain protected derivatives (e.g. alkyl, such as $C_{1-6}$ alkyl, for example tert-butyl, protected derivatives) of compounds of formula XXV in which $R^y$ represents —$C(O)NH_2$ may be prepared by reaction of a compound of formula XXVIII as hereinbefore defined, with a compound of formula XXIX, $R^ZN=C=O$      XXIX wherein $R^Z$ represents an appropriate protecting group, such as an alkyl group, including $C_{1-6}$ alkyl, e.g. tert-butyl, for example at low temperature (e.g. −78° C. to around 0° C.), in the presence of a suitable base (e.g. n-butyl lithium) and an appropriate solvent (e.g. THF).

(d) Certain protected derivatives (e.g. alkyl, such as $C_{1-6}$ alkyl, for example tert-butyl, protected derivatives) of compounds of formula XXV in which $R^y$ represents —C(O)NH$_2$ may also be prepared by reaction of a compound of formula XXX,

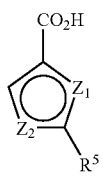

XXX wherein $R^5$, $Z_1$ and $Z_2$ are as hereinbefore defined with a protected (e.g. an (e.g. $C_{1-6}$) alkyl, such as tert-butyl-protected) derivative of ammonia (e.g. tert-butylamine) under standard coupling conditions (see, for example, those described hereinbefore for preparation of compounds of formula I (process step (iii))). Compounds of formula XXX are known in the art or may be prepared by way of standard techniques, for example oxidation of a corresponding compound of formula XXV in which $R^y$ is —CHO e.g. under those conditions described hereinbefore for preparation of compounds of formula V.

(e) Compounds of formula XXV in which $R^y$ is —CHO, $Z_1$ represents —CH=CH— and $Z_2$ represents —CH—, and protected derivatives thereof, may be prepared by reaction of a compound of formula XXVIII in which $Z_1$ represents —CH=CH— and $Z_2$ represents —CH— with an appropriate reagent system for the introduction of an aldehyde group into the benzene ring (e.g. Zn(CN)$_2$ and HCl or, preferably, TiCl$_4$/CHCl$_3$, SnCl$_4$/CH$_2$Cl$_2$ or 1,3,5,7-azaadamantane/TFA) under standard reaction conditions, followed by (if appropriate) protection of the resultant benzaldehyde under standard conditions.

(f) Compounds of formula XXV in which $R^y$ is —NH$_2$, $Z_1$ represents —CH=CH— and $Z_2$ represents —CH—, and N-protected derivatives thereof, may be prepared by nitration of a compound of formula XXVIII in which $Z_1$ represents —CH=CH— and $Z_2$ represents —CH—, followed by reduction of the resultant nitrobenzene and (if appropriate) protection of the resultant aminobenzene, all of which steps may be carried out under standard conditions.

Compounds of formulae III, IV, VI, VIII, X, XI, XII, XIII, XIV, XVIa, XXII, XXIIa, XXIII, XXVI, XXVII, XXVIII, XXIX and XXX are either commercially available, are known in the literature, or may be obtained either by analogy with the processes described herein, or by conventional synthetic procedures, in accordance with standard techniques, from readily available starting materials using appropriate reagents and reaction conditions.

Compounds of the invention may be isolated from their reaction mixtures using conventional techniques.

It will be appreciated by those skilled in the art that, in the processes described above and hereinafter, the functional groups of intermediate compounds may need to be protected by protecting groups.

Functional groups that it is desirable to protect include sulphonamido, amido, amino and aldehyde. Suitable protecting groups for sulphonamido, amido and amino include tert-butyloxycarbonyl, benzyloxycarbonyl, 2-trimethylsilylethoxycarbonyl (Teoc) or tert-butyl. Suitable protecting groups for aldehyde include alcohols, such as methanol or ethanol, and diols, such as 1,3-propanediol or, preferably, 1,2-ethanediol (so forming a cyclic acetal).

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques (e.g. using a protic acid or a Lewis acid such as trifluoroacetic acid, sulfuric acid, toluenesulfonic acid, boron trichloride or Sc(OTf)$_3$).

Persons skilled in the art will appreciate that, in order to obtain compounds of the invention in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", 3$^{rd}$ edition, T. W. Greene & P. G. M. Wutz, Wiley-Interscience (1999).

Medical and Pharmaceutical Uses

Compounds of the invention are useful because they possess pharmacological activity. The compounds of the invention are therefore indicated as pharmaceuticals.

According to a further aspect of the invention there is thus provided the compounds of the invention for use as pharmaceuticals.

In particular, compounds of the invention are agonists of AngII, more particularly, are agonists of the AT2 receptor, and, especially, are selective agonists of that sub-receptor, for example as may be demonstrated in the tests described below.

The compounds of the invention are thus expected to be useful in those conditions in which endogenous production of AngII is deficient and/or where an increase in the effect of AngII is desired or required.

The compounds of the invention are further expected to be useful in those conditions where AT2 receptors are expressed and their stimulation is desired or required.

The compounds of the invention are further indicated in the treatment of conditions characterised by vasoconstriction, increased cell growth and/or differentiation, increased cardiac contractility, increased cardiovascular hypertrophy, and/or increased fluid and electrolyte retention.

The compounds of the invention are further indicated in the treatment of stress-related disorders, and/or in the improvement of microcirculation and/or mucosa-protective mechanisms.

Thus, compounds of the invention are expected to be useful in the treatment of disorders, which may be characterised as indicated above, and which are of, for example, the gastrointestinal tract, the cardiovascular system, the respiratory tract, the kidneys, the eyes, the female reproductive (ovulation) system and the central nervous system (CNS).

Disorders of the gastrointestinal tract that may be mentioned include oesophagitis, Barrett's oesophagus, gastric ulcers, duodenal ulcers, dyspepsia (including non-ulcer dyspepsia), gastro-oesophageal reflux, irritable bowel syndrome (IBS), inflammatory bowel disease (IBD), pancreatitis, hepatic disorders (such as hepatitis), gall bladder disease, multiple organ failure (MOF) and sepsis. Other gastrointestinal disorders that may be mentioned include xerostomia, gastritis, gastroparesis, hyperacidity, disorders of the bilary tract, coelicia, Crohn's disease, ulcerative colitis, diarrhoea, constipation, colic, dysphagia, vomiting, nausea, indigestion and Sjögren's syndrome.

Disorders of the respiratory tract that may be mentioned include inflammatory disorders, such as asthma, obstructive lung diseases (such as chronic obstructive lung disease), pneumonitis, pulmonary hypertension and adult respiratory distress syndrome.

Disorders of the kidneys that may be mentioned include renal failure, nephritis and renal hypertension.

Disorders of the eyes that may be mentioned include diabetic retinopathy, premature retinopathy and retinal microvascularisation.

Disorders of the female reproductive system that may be mentioned include ovulatory dysfunction.

Cardiovascular disorders that may be mentioned include hypertension, cardiac hypertrophy, cardiac failure, artherosclerosis, arterial thrombosis, venous thrombosis, endothelial dysfunction, endothelial lesions, post-balloon dilatation stenosis, angiogenesis, diabetic complications, microvascular dysfunction, angina, cardiac arrhythmias, claudicatio intermittens, preeclampsia, myocardial infarction, reinfarction, ischaemic lesions, erectile dysfunction and neointima proliferation.

Disorders of the CNS that may be mentioned include cognitive dysfunctions, dysfunctions of food intake (hunger/satiety) and thirst, stroke, cerebral bleeding, cerebral embolus and cerebral infarction.

Compounds of the invention may also be useful in the modulation of growth metabolism and proliferation, for example in the treatment of hypertrophic disorders, prostate hyperplasia, autoimmune disorders, psoriasis, obesity, neuronal regeneration, the healing of ulcers, inhibition of adipose tissue hyperplasia, stem cell differentiation and proliferation, cancer (e.g. in the gastrointestinal tract, lung cancer, etc), apoptosis, tumours (generally) and hypertrophy, diabetes, neuronal lesions and organ rejection.

The compounds of the invention are indicated both in the therapeutic and/or prophylactic treatment of the above conditions.

According to a further aspect of the present invention, there is provided a method of treatment of a condition in which endogenous production of AngII is deficient, and/or a condition where an increase in the effect of AngII is desired or required, and/or a condition where AT2 receptors are expressed and their stimulation is desired or required, which method comprises administration of a therapeutically effective amount of a compound of the invention to a person suffering from, or susceptible to, such a condition.

The compounds of the invention will normally be administered orally, intravenously, subcutaneously, buccally, rectally, dermally, nasally, tracheally, bronchially, by any other parenteral route or via inhalation, in a pharmaceutically acceptable dosage form.

When the condition to be treated is multiple organ failure, preferred routes of administration are parenteral (e.g. by injection). Otherwise, the preferred route of administration for compounds of the invention is oral.

The compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like.

Such formulations may be prepared in accordance with standard and/or accepted pharmaceutical practice.

According to a further aspect of the invention there is thus provided a pharmaceutical formulation including a compound of the invention, in admixture with a pharmaceutically acceptable adjuvant, diluent or carrier.

Compounds of the invention may also be administered in combination with other AT2 agonists that are known in the art, as well as in combination with AT1 receptor antagonists that are known in the art, such as losartan, or in combination with an inhibitor of angiotensin converting enzyme (ACE).

According to a further aspect of the invention, there is provided a combination product comprising:

(A) a compound of the invention; and
(B) an AT1 receptor antagonist, or an ACE inhibitor,
wherein each of components (A) and (B) is formulated in admixture with a pharmaceutically-acceptable adjuvant, diluent or carrier.

Such combination products provide for the administration of compound of the invention in conjunction with an AT1 receptor antagonist, or an ACE inhibitor, and may thus be presented either as separate formulations, wherein at least one of those formulations comprises compound of the invention, and at least one comprises AT1 receptor antagonist, or ACE inhibitor, or may be presented (i.e. formulated) as a combined preparation (i.e. presented as a single formulation including compound of the invention and AT1 receptor antagonist or ACE inhibitor).

Thus, there is further provided:

(1) a pharmaceutical formulation including a compound of the invention and an AT1 receptor antagonist, or an ACE inhibitor, in admixture with a pharmaceutically-acceptable adjuvant, diluent or carrier; and
(2) a kit of parts comprising components:
(a) a pharmaceutical formulation including a compound of the invention, in admixture with a pharmaceutically-acceptable adjuvant, diluent or carrier; and
(b) a pharmaceutical formulation including an AT1 receptor antagonist, or an ACE inhibitor, in admixture with a pharmaceutically-acceptable adjuvant, diluent or carrier,
which components (a) and (b) are each provided in a form that is suitable for administration in conjunction with the other.

Depending upon the disorder and patient to be treated and the route of administration, the compounds of the invention may be administered at varying doses.

Although doses will vary from patient to patient, suitable daily doses are in the range of about 1 to 1000 mg per patient, administered in single or multiple doses. More preferred daily doses are in the range 2.5 to 250 mg per patient.

Individual doses of compounds of the invention may be in the range 1 to 100 mg. In any event, the physician, or the skilled person, will be able to determine the actual dosage which will be most suitable for an individual patient, which is likely to vary with the condition that is to be treated, as well as the age, weight, sex and response of the particular patient to be treated. The above-mentioned dosages are exemplary of the average case; there can, of course, be individual instances where higher or lower dosage ranges are merited, and such are within the scope of this invention.

Compounds of the invention have the advantage that they bind selectively to, and exhibit agonist activity at, the AT2 receptor. By compounds which "bind selectively" to the AT2 receptor, we include that the affinity ratio for the relevant compound (AT2:AT1) is at least 5:1, preferably at least 10:1 and more preferably at least 20:1.

The compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art.

Biological Tests

The following test procedures may be employed.

Test A

Receptor Binding Assay using Rat Liver Membrane $AT_1$ Receptor

Rat liver membranes were prepared according to the method of Dudley et al (*Mol. Pharmacol.* (1990) 38, 370). Binding of [$^{125}$I]Ang II to membranes was conducted in a final volume of 0.5 mL containing 50 mM Tris-HCl (pH 7.4), 100 mM NaCl, 10 mM $MgCl_2$, 1 mM EDTA, 0.025% bacitracin, 0.2% BSA (bovine serum albumin), liver homogenate corresponding to 5 mg of the original tissue weight, [$^{125}$I]Ang II (70 000 cpm, 0.03 nM) and variable concentrations of test substance. Samples were incubated at 25° C. for 1 h, and binding was terminated by filtration through Whatman GF/B glass-fiber filter sheets using a Brandel cell harvester. The filters were washed with 4×2 mL of Tris-HCl (pH 7.4) and transferred to tubes. The radioactivity was measured in a gamma counter. The characteristics of the Ang II binding $AT_1$ receptor were determined by using six different concentrations (0.03-5 nmol/L) of the labeled [$^{125}$I]AngII. Non-specific binding was determined in the presence of 1 µM Ang II. The specific binding was determined by subtracting the non-specific binding from the total bound [$^{125}$I]AngII. The dissociation constant ($K_d$=1.7±0.1 nM, [L]=0.057 nM) was determined by Scatchard analysis of data obtained with Ang II by using GraFit (Erithacus Software, UK). The binding data were best fitted with a one-site fit. All experiments were performed at least in triplicate.

Test B

Receptor Binding Assay using Porcine Myometrial Membrane AT7 Receptor

Myometrial membranes were prepared from porcine uteri according to the method by Nielsen et al (*Clin. Exp. Pharm. Phys.* (1997) 24, 309). Any possible interference that may be exhibited by binding of compound to $AT_1$ receptors was blocked by addition of 1 µM of a selective AT1 inhibitor. Binding of [$^{125}$I]Ang II to membranes was conducted in a final volume of 0.5 mL containing 50 mM Tris-HCl (pH 7.4), 100 mM NaCl, 10 mM $MgCl_2$, 1 mM EDTA, 0.025% bacitracin, 0.2% BSA, homogenate corresponding to 10 mg of the original tissue weight, [$^{125}$I]Ang II (70 000 cpm, 0.03 nM) and variable concentrations of test substance. Samples were incubated at 25° C. for 1 h, and binding was terminated by filtration through Whatman GF/B glass-fiber filter sheets using a Brandel cell harvester. The filters were washed with 3×3 mL of Tris-HCl (pH 7.4) and transferred to tubes. The radioactivity was measured using a gamma counter. The characteristics of the Ang II binding $AT_2$ receptor was determined by using six different concentrations (0.03-5 nmol/L) of the labeled [$^{125}$I]Ang II. Non-specific binding was determined in the presence of 1 µM Ang II. The specific binding was determined by subtracting the non-specific binding from the total bound [$^{125}$I]Ang II. The dissociation constant ($K_d$=0.7±0.1 nM, [L]=0.057 nM) was determined by Scatchard analysis of data obtained with Ang II by using GraFit (Erithacus Software, UK). The binding data were best fitted with a one-site fit. All experiments were performed at least in triplicate.

Test C

Duodenal Mucosal Alkaline Secretion Assay

Compounds were exposed to the duodenal mucosa in barbiturate-anaesthetised rats prepared for in situ titration of duodenal mucosal alkaline secretion, according to the methodology described by Flemström et al in *Am. J. Physiol.* (1982) 243, G348.

The invention is illustrated by way of the following examples.

EXAMPLE 1

N-Butyloxycarbonyl-3-(4-imidazol-1-ylmethylphenyl)-5-iso-butylthio-phene-2-sulfonamide (a) N-tert-Butylthiophene-2-sulfonamide Thiophene-2-sulfonyl chloride (15 g, 0.082 mol) was dissolved in $CHCl_3$ (200 mL) under $N_2$ atmosphere and then cooled to 0° C. tert-Butylamine (25.9 mL, 0.246 mol) dissolved in $CHCl_3$ (50 mL) was then added dropwise to the reaction mixture. The reaction mixture was stirred for 1 h at room temperature and then at reflux for 10 min. Toluene (700 mL) was added and the organic phase was washed with water (3×50 mL), dried, and concentrated in vacuo. The sub-title product was used without further purification in the next step.

$^1$H NMR δ ($CDCl_3$): 7.60 (1H, dd, J=1.3, 3.8 Hz), 7.53 (1H, dd, J=1.3, 5.0 Hz), 7.02 (1H, dd, J=5.0, 3.8 Hz), 5.13 (1H, m), 1.24 (9H, m).

$^{13}$C NMR δ ($CDCl_3$): 145.0, 131.7, 131.2, 127.0, 55.1, 29.9.

(b) 5-iso-Butyl-N-tert-butylthiophene-2-sulfonamide

N-tert-Butylthiophene-2-sulfonamide (10 g, 0.046 mol, see step (a) above) was dissolved in THF (85 mL) under $N_2$ and then cooled to −78° C. n-BuLi (1.6 M, 76.9 mL, 0.12 mol) was added via a syringe. The reaction mixture was stirred at −78° C. for 30 min. and then at −40° C. for 2 h. Iodo-2-methylpropane (10.5 mL, 0.09 mol) was added dropwise to the reaction mixture. The reaction mixture was stirred overnight at room temperature. The reaction was quenched with $NH_4Cl$ (aq.) and extracted with EtOAc. The combined organic phase was washed with brine and dried and concentrated in vacuo. The crude product was purified on column chromatography (hexanes:EtOAc (10:1)) to give the sub-title compound in 55% yield (7.0 g, 0.025 mol).

$^1$H NMR δ ($CDCl_3$): 7.43 (1H, d, J=3.6 Hz), 6.67 (1H, d, J=3.8 Hz), 4.83 (1H, m), 2.67 (2H, d, J=7 Hz), 1.88 (1H, m), 1.26 (9H, m), 0.93 (6H, J=6.6 Hz).

$^{13}$C NMR δ ($CDCl_3$): 145.0, 131.7, 131.2, 127.0, 55.1, 29.9.

(c) 5-iso-Butyl-2-(N-tert-butylaminosulfonyl)thiol-phene-3-boronic acid 5-iso-Butyl-N-tert-butylthiophene-2-sulfonamide (10.6 g, 0.039 mol, see step (b) above) was dissolved in THF (165 mL) under $N_2$ and then cooled to −78° C. n-BuLi (1.6 M, 60.19 mL, 0.096 mol) was added via a syringe. The reaction mixture was stirred at −20° C. for 4 h. The tri-iso-propylborate (13.3 mL, 0.058 mol) was then added via a syringe and the reaction mixture was stirred overnight at room temperature. The reaction was quenched with 2 M HCl (20 mL). The organic phase was separated and the water phase was extracted with EtOAc (3×100 mL). The combined organic phase was washed with brine, dried and concentrated in vacuo. The product was used without further purification.

MS (ESI$^+$) m/z: 236.8

(d) 3-(3-Hydroxymethylphenyl)-5-iso-butyl-N-tert-butylthiophene-2-sulfonamide A mixture of m-bromobenzyl alcohol (1.05 g, 5.80 mmol), 5-iso-butyl-2-(N-tert-butylaminosulfonyl)thiophene-3-boronic acid (2.41 g, 7.55 mmol; see step (c)), Pd(PPh$_3$)$_4$ (270 mg, 0.235 mmol), NaOH (19.1 mL, 1.5 M aq, 28.6 mmol), EtOH (5.0 mL) and toluene (30 mL) was stirred under N$_2$ at 90° C. for about 4 h. After cooling, water (10 mL) was added to the reaction mixture and this was then extracted with ethyl acetate. The combined organic phase was dried and concentrated in vacuo. The crude product was purified on column chromatography (EtOAc/hexane, 30:70) to give sub-title compound as a colourless syrup in 57% yield (1.26 g, 3.31 mmol).

$^1$H NMR δ (CDCl$_3$): 0.96 (d, J=6.6 Hz, 6H), 0.98 (s, 9H), 1.82-2.00 (m, 1H), 2.66 (d, J=7.1 Hz, 2H), 3.28 (br s, 1H), 4.67 (s, 2H), 4.81 (br s, 1H), 6.76 (s, 1H), 7.30-7.50 (m, 3H), 7.64 (s, 1H).

$^{13}$C NMR δ (CDCl$_3$): 22.1, 29.4, 30.4, 39.1, 54.4, 64.6, 127.1, 127.8, 128.5, 129.0, 134.9, 136.2, 141.2, 143.2, 148.2.

MS (ESI) m/z: 382 (M+1)$^+$.

IR σ (neat, cm$^{-1}$): 3498, 3286, 2958, 2870, 1465, 1313.

Anal. Calcd. for C$_{19}$H$_{27}$NO$_3$S$_2$: C, 59.81; H, 7.13; N, 3.67. Found: C, 60.05; H, 7.31; N, 3.90.

(e) 3-(3-Bromomethylphenyl)-5-iso-butyl-N-tert-butylthiophene-2-sulfonamide

A mixture of 3-(3-hydroxymethylphenyl)-5-iso-butyl-N-tert-butylthiophene-2-sulfonamide (246 mg, 0.644 mmol; see step (d)), CBr$_4$ (534 mg, 1.61 mmol) and PPh$_3$ (422 mg, 1.61 mmol) in DMF (5.0 mL) was stirred at room temperature overnight. Water (10 mL) was then added and the reaction mixture was extracted with ethyl acetate. The combined organic phase was washed with water, dried and concentrated in vacuo. The crude product was purified on column chromatography (Hex/EtOAc 9:1) to give the sub-title compound as a white solid in 95% yield (273 mg, 0.612 mmol).

$^1$H NMR δ (CDCl$_3$): 0.97 (d, J=6.3 Hz, 6H), 0.98 (s, 12H), 1.84-2.00 (m, 1H), 2.69 (d, J=7.1 Hz, 2H), 4.18 (br s, 1H), 4.54 (s, 2H), 6.78 (s, 1H), 7.37-7.44 (2H, m), 7.50-7.56 (m, 1H), 7.69 (br s, 1H).

$^{13}$C NMR δ (CDCl$_3$): 22.2, 29.5, 30.5, 33.3, 39.2, 54.4, 128.6, 128.8, 128.97, 129.02, 129.7, 135.5, 136.8, 138.3, 142.1, 148.5.

MS (ESI) m/z: 444 (M+H)$^+$, 446 ((M+H)$^+$+2).

IR ν (neat, cm$^{-1}$): 3296, 2969, 2870, 1586, 1452, 1303.

Anal. Calcd. for C$_{19}$H$_{26}$BrNO$_2$S$_2$: C, 51.34; H, 5.90; N, 3.15. Found: C, 51.44; H, 6.02; N, 3.22.

(f) 3-(3-Imidazol-1-ylmethylphenyl)-5-iso-butyl-N-tert-butylthiophene-2-sulfonamide To a solution of 3-(3-bromomethylphenyl)-5-iso-butyl-N-tert-butylthiophene-2-sulfonamide (58 mg, 0.13 mmol; see step (e)) in dioxane (2.0 mL) was added imidazole (22 mg, 0.33 mmol) and the reaction mixture was stirred for 1 h at 80° C. The reaction mixture was concentrated in vacuo and the residue was purified by flash chromatography using MeOH:CH$_2$Cl$_2$ (5:95) as eluent to give the sub-title compound in 68% yield as a colourless syrup (38.4 mg, 0.088 mmol).

$^1$H NMR δ (CDCl$_3$): 0.85-1.05 (m, 15H), 1.80-2.00 (m, 1H), 2.66 (d, J=7.1 Hz, 2H), 4.38 (s, 1H), 5.19 (s, 2H), 6.72 (s, 1H), 6.99 (s, 1H), 7.10 (s, 1H), 7.22 (apparent d, J=7.6 Hz, 1H), 7.41 (apparent t, J=7.6 Hz, 1H), 7.47-7.55 (m, 2H), 7.82 (s, 1H).

$^{13}$C NMR δ (CDCl$_3$): 22.1, 29.5, 30.5, 39.1, 51.0, 54.5, 119.3, 127.4, 128.4, 128.9, 128.7, 129.1, 135.6, 136.2, 136.7, 137.1, 142.3, 148.6.

MS (ESI) m/z: 432 (M+H)$^+$.

IR ν (neat, cm$^{-1}$): 3287, 3063, 2961, 1439, 1311.

Anal. Calcd. for C$_{22}$H$_{29}$N$_3$O$_2$S$_2$: C, 61.22; H, 6.77; N, 9.74. Found: C, 61.04; H, 6.60; N, 9.82.

(g) N-Butyloxycarbonyl-3-(3-(imidazol-1-ylmethylphenyl)-5-iso-butylthiophene-2-sulfonamide To a solution of 3-(3-imidazol-1-ylmethylphenyl)-5-iso-butyl-N-tert-butylthiophene-2-sulfonamide (68.8 mg, 0.159 mmol; see step (f)) in CH$_2$Cl$_2$ (2 mL) was added BCl$_3$ (0.6 mL, 1.0 M in hexane) and the reaction mixture was stirred for 1 h at ambient temperature. The reaction mixture was concentrated in vacuo. Water (5 mL) was added to the residue and this was then extracted with EtOAc. The combined organic phase was washed with water and brine and dried over anhydrous MgSO$_4$, concentrated in vacuo. To the crude product dissolved in pyridine (1.5 mL) was added pyrrolidinopyridine (69.8 mg, 0.471 mmol) and butyl chloroformate (202.8 μL, 1.59 mmol) and the reaction mixture was stirred overnight. Citric acid (3 mL, 10% aq) was added to the reaction mixture, extracted with EtOAc, dried (over anhydrous MgSO$_4$), concentrated in vacuo, and the residue was purified by flash chromatography using MeOH:CH$_2$Cl$_2$ (6:94) as eluent to give the title compound in 59% yield, over two steps, (44.4 mg, 0.093 mmol).

$^1$H NMR δ (CDCl$_3$): 0.86 (t, J=7.3 Hz, 3H), 0.97 (d, J=6.6 Hz, 6H), 1.18-1.34 (m, 2H), 1.44-1.58 (m, 2H), 1.84-2.00 (m, 1H), 2.67 (d, J=7.1 Hz, 2H), 4.01 (t, J=6.6 Hz, 2H), 4.93 (s, 2H), 6.69 (s, 1H), 6.76-7.10 (m, 3H), 7.17 (apparent t, J=7.6 Hz, 1H), 7.32 (d, J=7.6 Hz, 1H), 7.52 (s, 1H), 7.61 (br s, 1H), 12.9 (br s, 1H).

$^{13}$C NMR δ (CDCl$_3$): 13.7, 18.9, 22.2, 30.4, 30.7, 39.2, 51.1, 65.7, 119.6, 125.6, 126.5, 128.5, 128.8, 129.0, 129.3, 134.1, 134.7, 135.6, 136.2, 143.6, 149.7, 153.5.

IR ν (neat, cm$^{-1}$): 3130, 3057, 2958, 1740, 1656, 1450, 1344.

MS (ESI) m/z: 476 (M+H)$^+$.

Anal. Calcd. for C$_{23}$H$_{29}$N$_3$O$_4$S$_2$: C, 58.08; H, 6.15; N, 8.83. Found: C, 57.87; H, 6.14; N, 8.74.

EXAMPLE 2

N-Butyloxycarbonyl-3-[3-(2-methylimidazol-1-ylmethyl)phenyl]-5-iso-butylthio-phene-2-sulfonamide

(a) 3-[3-(2-Methylimidazol-1-ylmethyl)phenyl]-5-iso-butyl-N-tert-butylthiophene-2-sulfonamide To a solution of 3-(3-bromomethylphenyl)-5-iso-butyl-N-tert-butylthiophene-2-sulfonamide (105 mg, 0.236 mmol; see Example 1(e)) in dioxane (2.0 mL) was added 2-methylimidazole (58 mg, 0.71 mmol) and the reaction mixture was stirred for 1.5 h at 80° C. The reaction mixture was concentrated in vacuo and the residue was purified by flash chromatography using MeOH:CH$_2$Cl$_2$ (6:94) as eluent to give the sub-title compound in 77% yield as a colourless syrup (81 mg, 0.182 mmol).

¹H NMR δ (CDCl₃): δ 0.90-1.10 (m, 15H), 1.80-2.00 (m, 1H), 2.41 (s, 3H), 2.66 (d, J=7.1 Hz, 2H), 4.27 (br s, 1H), 5.10 (s, 2H), 6.71 (s, 1H), 6.94 (br s, 1H), 6.97 (br s, 1H), 7.10 (br d, J=7.6 Hz, 1H), 7.40 (apparent t, J=7.6 Hz, 1H), 7.44 (br s, 1H), 7.50 (m, 1H).
¹³C NMR δ (CDCl₃): 12.8, 22.1, 29.5, 30.5, 39.1, 49.8, 54.5, 119.9, 126.3, 126.8, 127.9, 128.6, 128.8, 129.0, 135.7, 136.2, 136.6, 142.3, 144.7, 148.6.
IR ν (neat, cm⁻¹): 3262, 3060, 2960, 2869, 1603, 1433, 1391, 1310.
MS (ESI) m/z: 446 (M+H)⁺.
Anal. Calcd. for $C_{23}H_{31}N_3O_2S_2$: C, 61.99; H, 7.01; N, 9.43. Found: C, 61.77; H, 7.18; N, 9.34.

(b) N-Butyloxycarbonyl-3-[3-(2-methylimidazol-1-ylmethyl)phenyl]-5-iso-butyl-thiophene-2-sulfonamide To a solution of 3-[3-(2-methylimidazol-1-ylmethyl)phenyl]-5-iso-butyl-N-tert-butylthiophene-2-sulfonamide (46.5 mg, 0.104 mmol; see step (a)) in CH₂Cl₂ (1 mL) was added BCl₃ (0.5 mL, 1.0 M in hexane) and the reaction mixture was stirred for 1 h at ambient temperature. The reaction mixture was concentrated in vacuo. Water (5 mL) was added to the residue and this was then extracted with EtOAc. The combined organic phase was washed with water and brine, dried (over anhydrous MgSO₄) and concentrated in vacuo. To the crude product dissolved in CH₂Cl₂ (5 mL) was added Na₂CO₃ (49.6 mg, 0.467 mmol), water (2 mL) and butyl chloroformate (14.5 μL, 0.114 mmol), and the reaction mixture was stirred for 2 h at ambient temperature. The reaction mixture was diluted with CH₂Cl₂ (30 mL) and washed with citric acid (10% aq), brine, water, dried (over anhydrous MgSO₄), concentrated in vacuo, and the residue purified by LCMS (Liquid Chromatography Mass Spectrum; 20-100% CH₃CN in water) to give the title compound in 65% yield, over two steps, (33.2 mg, 0.0678 mmol).
¹H NMR δ (CDCl₃): 0.84 (t, J=7.2 Hz, 3H), 0.94 (d, J=6.6 Hz, 6H), 1.16-1.33 (m, 2H), 1.42-1.55 (m, 2H), 1.80-1.98 (m, 1H), 2.40 (s, 3H), 2.62 (d, J=6.9 Hz, 2H), 3.94 (t, J=6.7 Hz, 2H), 4.98 (s, 2H), 6.64 (s, 1H), 6.86 (d, J=1.6 Hz, 1H), 6.95 (d, J=7.7 Hz, 1H), 7.01 (d, J=1.6 Hz, 1H), 7.14 (apparent t, J=7.7 Hz, 1H), 7.43 (d, J=7.7 Hz, 1H), 7.52 (s, 1H), 12.04 (br s, 1H).
¹³C NMR δ (CDCl₃): 10.9, 13.8, 19.0, 22.3, 30.4, 31.0, 39.2, 50.6, 64.9, 120.5, 120.7, 126.6, 128.4, 129.46, 129.49, 133.1, 136.7, 137.7, 141.4, 143.7, 147.3, 157.1.
IR ν (neat, cm⁻¹): 3145, 3058, 2958, 2871, 1664, 1611, 1455, 1386.
MS (ESI) m/z: 490 (M+H)⁺.
Anal. Calcd. for $C_{24}H_{31}N_3O_4S_2$: C, 58.87; H, 6.38; N, 8.58. Found: C, 58.70; H, 6.58; N, 8.45.

EXAMPLE 3

N-Butyloxycarbonyl-3-(3-benzoimidazol-1-ylmethylphenyl)-5-iso-butylthio-phene-2-sulfonamide (a) 3-(3-Benzoimidazol-1-ylmethylphenyl)-5-isobutyl-N-tert-butylthiophene-2-sulfonamide To a solution of 3-(3-bromomethylphenyl)-5-iso-butyl-N-tert-butylthiophene-2-sulfonamide (71.8 mg, 0.162 mmol; see Example 1(e)) in dioxane (2.0 mL) was added benzimidazole (57.3 mg, 0.485 mmol) and the reaction mixture was stirred for 5.5 h at 80° C. The reaction mixture was concentrated in vacuo and the residue was purified by flash chromatography using MeOH:CH₂Cl₂ (3:97) as eluent to give the sub-title compound in 93% yield as a colourless syrup (72.3 mg, 0.151 mmol).
¹H NMR δ (CDCl₃): 0.85 (s, 9H), 0.94 (d, J=6.6 Hz, 6H), 1.80-2.00 (m, 1H), 2.64 (d, J=6.9 Hz, 2H), 4.39 (brs, 1H), 5.46 (s, 2H), 6.70 (s, 1H), 7.20-7.34 (m, 3H), 7.34-7.54 (m, 3H), 7.60 (s, 1H), 7.76-7.90 (m, 1H), 8.42 (br s, 1H).
¹³C NMR δ (CDCl₃): 22.1, 29.3, 30.4, 39.1, 49.0, 54.4, 110.4, 119.8, 123.0, 123.7, 127.2, 128.2, 128.76, 128.83, 129.1, 133.1, 135.5, 135.6, 136.7, 142.0, 142.2, 142.9, 148.5.
IR ν (neat, cm⁻¹): 3275, 3059, 2971, 2869, 1496, 1459, 1367.
MS (ESI) m/z: 482 (M+H)⁺.
Anal. Calcd. for $C_{26}H_{31}N_3O_2S_2 \cdot \frac{1}{2}H_2O$: C, 63.64; H, 6.57; N, 8.56. Found: C, 63.66; H, 6.30; N, 8.72.

(b) N-Butyloxycarbonyl-3-(3-benzoimidazol-1-ylmethylphenyl)-5-iso-butylthio-phene-2-sulfonamide To a solution of 3-(3-benzoimidazol-1-ylmethylphenyl)-5-iso-butyl-N-tert-butylthiophene-2-sulfonamide (67.6 mg, 0.14 mmol; see step (a)) in CH₂Cl₂ (2 mL) was added BCl₃ (0.6 mL, 1.0 M in hexane) and the reaction mixture was stirred for 1 h at ambient temperature. The reaction mixture was concentrated in vacuo. Water (5 mL) was added to the residue and this was then extracted with EtOAc. The combined organic phase was washed with water and brine, dried (over anhydrous MgSO₄) and concentrated in vacuo. To the crude product dissolved in pyridine (1.5 mL) was added pyrrolidinopyridine (41.6 mg, 0.28 mmol) and butyl chloroformate (178.4 μL, 1.40 mmol) and the reaction mixture was stirred overnight. Citric acid (3 mL, 10% aq.) was added to the reaction mixture, which was then extracted with EtOAc, dried (over anhydrous MgSO₄), concentrated in vacuo, and the residue purified by flash chromatography using MeOH:CH₂Cl₂ (5:95) as eluent to give the title compound in 70% yield, over two steps, (51.6 mg, 0.098 mmol).
¹H NMR δ (CDCl₃): 0.84 (t, J=7.3 Hz, 3H), 0.98 (d, J=6.6 Hz, 6H), 1.15-1.35 (m, 2H), 1.45-1.60 (m, 2H), 1.85-2.00 (m, 1H), 2.68 (d, J=6.8 Hz, 2H), 4.06 (t, J=6.7 Hz, 2H), 5.34 (s, 2H), 6.72 (s, 1H), 7.02 (d, J=7.4 Hz, 1H), 7.19 (apparent t, J=7.6 Hz, 1H), 7.30 (d, J=7.7 Hz, 1H), 7.32-7.50 (m, 3H), 7.59 (s, 1H), 7.87 (br s, 1H), 8.79 (br s, 1H), 9.00 (br s, 1H).
¹³C NMR δ (CDCl₃): 13.7, 18.8, 22.2, 30.47, 30.54, 39.3, 49.5, 66.3, 111.5, 118.1, 124.7, 125.0, 126.9, 128.6, 128.8, 129.0, 132.0, 132.3, 134.1, 135.1, 136.8, 142.4, 144.5, 150.9, 151.4.
IR(CM⁻¹): 2959, 1740, 1459, 1343.
MS (ESI) m/z: 526 (M+H)⁺.
Anal. Calcd. for $C_{27}H_{31}N_3O_4S_2$: C, 61.69; H, 5.94; N, 7.99. Found: C, 61.51; H, 6.07; N, 7.78.

EXAMPLE 4

N-Butyloxycarbonyl-3-(3-pyrazol-1-ylmethylphenyl)-5-iso-butylthiophene-2-sulfonamide (a) 3-(3-Pyrazol-1-ylmethylphenyl)-5-iso-butyl-N-tert-butylthiophene-2-sulfonamide To a solution of 3-(3-bromomethylphenyl)-5-iso-butyl-N-tert-butylthiophene-2-sulfonamide (90.4 mg, 0.203 mmol; see Example 1(e)) in dioxane (2.0 mL) was added pyrazole (41.5 mg, 0.609 mmol) and the reaction mixture was stirred for 18 h at 80° C., after which another portion of pyrazole (60.4 mg, 0.887 mmol) was added and the reaction mixture stirred for a further 3 h. The reaction mixture was concentrated in vacuo and the residue was purified by flash chromatography using EtOAc:petroleum ether (2:8) as eluent to give the sub-title compound in 98% yield as a colourless syrup (86 mg, 0.199 mmol).

$^1$H NMR δ (CDCl$_3$): 0.87 (s, 9H), 0.96 (d, J=6.6 Hz, 6H), 1.82-2.00 (m, 1H), 2.67 (d, J=7.1 Hz, 2H), 5.04 (br s, 1H), 5.30 (s, 2H), 6.28 (s, 1H), 6.78 (s, 1H), 7.27-7.34 (m, 1H), 7.39 (apparent t, J=7.4 Hz, 1H), 7.45 (apparent dt, J=7.4, 1.5 Hz, 1H), 7.48-7.56 (m, 2H), 7.78 (s, 1H).

$^{13}$C NMR δ (CDCl$_3$): 22.1, 29.3, 30.4, 39.1, 54.1, 55.7, 105.9, 127.9, 128.2, 128.3, 128.8, 129.6, 135.2, 136.5, 137.2, 140.0, 141.8, 148.1.

IR ν (neat, cm$^{-1}$): 3253, 3150, 2961, 2871, 1320.

MS (ESI) m/z: 432 (M+H)$^+$.

Anal. Calcd. for C$_{22}$H$_{29}$N$_3$O$_2$S$_2$: C, 61.22; H, 6.77; N, 9.74. Found: C, 61.11; H, 6.59; N, 9.86.

(b) N-Butyloxycarbonyl-3-(3-pyrazol-1-ylmethylphenyl)-5-iso-butylthiophene-2-sulfonamide To a solution of 3-(3-pyrazol-1-ylmethylphenyl)-5-iso-butyl-N-tert-butylthiophene-2-sulfonamide (82.4 mg, 0.191 mmol; see step (a)) in CH$_2$Cl$_2$ (2 mL) was added BCl$_3$ (0.6 mL, 1.0 M in hexane) and the reaction mixture was stirred for 1 h at ambient temperature. The reaction mixture was concentrated in vacuo. Water (5 mL) was added to the residue and this was then extracted with EtOAc. The combined organic phase was washed with water and brine, dried (over anhydrous MgSO$_4$) and concentrated in vacuo. To the crude product dissolved in pyridine (1.5 mL) was added pyrrolidinopyridine (42.7 mg, 0.288 mmol) and butyl chloroformate (192.6 µL, 1.91 mmol) and the reaction mixture was stirred overnight. Citric acid (5 mL, 10% aq) was added to the reaction mixture, which was then extracted with EtOAc, dried (over anhydrous MgSO$_4$), concentrated in vacuo, and the residue was purified by LCMS (30-100% CH$_3$CN in water) to give the title compound in 69% yield, over two steps, (62.7 mg, 0.132 mmol).

$^1$H NMR δ (CDCl$_3$): 0.78 (t, J=7.1 Hz, 3H), 0.99 (d, J=6.6 Hz, 6H), 1.02-1.16 (m, 2H), 1.28-1.44 (m, 2H), 1.86-2.04 (m, 1H), 2.71 (d, J=7.1 Hz, 2H), 3.88 (t, J=6.5 Hz, 2H), 5.25 (s, 2H), 6.26 (s, 1H), 6.87 (s, 1H), 7.22-7.42 (3H, m), 7.51 (s, 1H), 7.55 (s, 1H), 7.95 (s, 1H), 10.42 (br s, 1H).

$^{13}$C NMR δ (CDCl$_3$): 13.5, 18.6, 22.2, 30.2, 30.5, 39.3, 55.7, 66.1, 105.5, 128.0, 128.04, 128.3, 128.9, 129.8, 130.6, 132.3, 134.2, 135.6, 140.2, 144.1, 150.7, 150.8.

IR ν (neat, cm$^{-1}$): 2959, 2931, 2872, 1746, 1346.

MS (ESI) m/z: 476 (M+H)$^+$.

Anal. Calcd. for C$_{23}$H$_{29}$N$_3$O$_4$S$_2$: C, 58.08; H, 6.15; N, 8.83. Found: C, 58.03; H, 6.41; N, 8.65.

EXAMPLE 5

N-Butyloxycarbonyl-3-[3-(2-ethylimidazol-1-ylmethyl)phenyl]-5-iso-butylthio-phene-2-sulfonamide (a) 3-[3-(2-Ethylimidazol-1-ylmethyl)phenyl]-5-iso-butyl-N-tert-butylthiophene-2-sulfonamide To a solution of 3-(3-bromomethylphenyl)-5-iso-butyl-N-tert-butylthiophene-2-sulfonamide (70 mg, 0.158 mmol; see Example 1(e)) in dioxane (2.0 mL) was added 2-ethylimidazole (45.4 mg, 0.473 mmol) and the reaction mixture was stirred for 1 h at 80° C. The reaction mixture was concentrated in vacuo and the residue was purified by flash chromatography using MeOH:CH$_2$Cl$_2$ (6:94) as eluent to give the sub-title compound in 85% yield as a colourless syrup (61.2 mg, 0.134 mmol).

$^1$H NMR δ (CDCl$_3$): 0.95 (s, 9H), 0.96 (d, J=6.5 Hz, 6H), 1.29 (t, J=7.3 Hz, 3H), 1.80-1.98 (m, 1H), 2.58-2.72 (m, 4H), 4.11 (br s, 1H), 5.08 (s, 2H), 6.70 (s, 1H), 6.88 (s, 1H), 6.98 (s, 1H), 7.08 (d, J=7.7 Hz, 1H), 7.39 (apparent t, J=7.7 Hz, 1H), 7.42 (s, 1H), 7.51 (d, J=7.7 Hz, 1H).

$^{13}$C NMR δ (CDCl$_3$): 11.9, 20.2, 22.1, 29.4, 30.5, 39.1, 49.1, 54.5, 119.6, 126.7, 127.5, 127.7, 128.5, 128.7, 129.0, 135.5, 136.6, 136.9, 142.3, 148.5, 149.4.

IR ν (neat, cm$^{-1}$): 3283, 3053, 2966, 2870, 1493, 1465, 1430, 1313.

MS (ESI) m/z: 460 (M+H)$^+$.

Anal. Calcd. for C$_{24}$H$_{33}$N$_3$O$_2$S$_2$·½H$_2$O: C, 61.50; H, 7.31; N, 8.97. Found: C, 61.53; H, 7.36; N, 8.99.

(b) N-Butyloxycarbonyl-3-[3-(2-ethylimidazol-1-ylmethyl)phenyl]-5-iso-butyl-thiophene-2-sulfonamide To a solution of 3-[3-(2-ethylimidazol-1-ylmethyl)phenyl]-5-iso-butyl-N-tert-butylthiophene-2-sulfonamide (55.1 mg, 0.120 mmol; see step (a)) in CH$_2$Cl$_2$ (2 mL) was added BCl$_3$ (0.6 mL, 1.0 M in hexane) and the reaction mixture was stirred for 1 h at ambient temperature. The reaction mixture was concentrated in vacuo. Water (5 mL) was added to the residue and this was then extracted with EtOAc. The combined organic phase was washed with water and brine, dried over anhydrous MgSO$_4$, concentrated in vacuo. To the crude product dissolved in pyridine (1.5 mL) was added pyrrolidinopyridine (35.5 mg, 0.240 mmol) and butyl chloroformate (152.5 µL, 1.20 mmol) and the reaction mixture was stirred overnight. Citric acid (3 mL, 10% aq) was added to the reaction mixture, extracted with EtOAc, dried (over anhydrous MgSO$_4$), concentrated in vacuo, and the residue was purified by flash chromatography using MeOH:CH$_2$Cl$_2$ (5:95 to 8:92) as eluent to give the title compound in 73% yield, over two steps, (44.3 mg, 0.088 mmol).

$^1$H NMR δ (CDCl$_3$): 0.84 (t, J=7.3 Hz, 3H), 0.94 (d, J=6.6 Hz, 6H), 1.15 (t, J=7.6 Hz, 3H), 1.19-1.35 (m, 2H), 1.40-1.55 (m, 2H), 1.80-1.98 (m, 1H), 2.63 (d, J=6.9 Hz, 2H), 2.85 (q, J=7.4 Hz, 2H), 3.94 (t, J=6.8 Hz, 2H), 5.02 (s, 2H), 6.64 (s, 1H), 6.81 (d, J=1.6 Hz, 1H), 6.97 (d, J=7.7 Hz, 1H), 7.01 (s, 1H), 7.16 (apparent t, J=7.7 Hz, 1H), 7.45 (d, J=7.7 Hz, 1H), 7.56 (s, 1H), 12.4 (br s, 1H).

$^{13}$C NMR δ (CDCl$_3$): 12.2, 13.7, 18.5, 19.0, 22.3, 30.4, 30.9, 39.2, 50.3, 65.0, 120.6, 121.2, 126.6, 128.3, 128.4, 129.5, 129.6, 133.3, 136.7, 137.6, 141.4, 147.4, 148.0, 157.1.

IR ν (neat, cm$^{-1}$): 3139, 3054, 2959, 2871, 1664, 1608, 1464, 1386, 1266.

MS (ESI) m/z: 504 (M+H)$^+$.

Anal. Calcd. for C$_{25}$H$_{33}$N$_3$O$_4$S$_2$: C, 59.61; H, 6.60; N, 8.34. Found: C, 59.30; H, 6.59; N, 8.15.

EXAMPLE 6

N-Butyloxycarbonyl-3-[3-(2-butylimidazol-1-ylmethyl)phenyl]-5-iso-butylthio-phene-2-sulfonamide (a) 2-Butyl-1H-imidazole The title compound was made prepared in accordance with a literature method (*Journal of Organic Chemistry* 1980, 45, 4038-4040).

(b) 3-[3-(2-Butylimidazol-1-ylmethyl)phenyl]-5-iso-butyl-N-tert-butylthiophene-2-sulfonamide To a solution of 3-(3-bromomethylphenyl)-5-iso-butyl-N-tert-butylthiophene-2-sulfonamide (70 mg, 0.158 mmol; see Example 1(e)) in dioxane (2.0 mL) was added 2-butylimidazole (58.7 mg, 0.473 mmol) and the reaction mixture was stirred for 1 h at 80° C. The reaction mixture was concentrated in vacuo and the residue was purified by flash chromatography using MeOH:CH$_2$Cl$_2$ (5:95) as eluent to give the sub-title compound in 55% yield as a colourless syrup (42.1 mg, 0.087 mmol).

$^1$H NMR δ (CDCl$_3$): 0.90 (t, J=7.4 Hz, 3H), 0.95 (d, J=6.4 Hz, 6H), 0.96 (s, 9H), 1.30-1.46 (m, 2H), 1.64-1.78 (m, 2H), 1.82-1.98 (m, 1H), 2.64 (t, J=7.4 Hz, 2H), 2.66 (d, J=7.1 Hz, 2H), 4.06 (br s, 1H), 5.08 (s, 2H), 6.70 (s, 1H), 6.87 (d, J=1.2 Hz, 1H), 6.98 (d, J=1.2 Hz, 1H), 7.08 (d, J=7.9 Hz, 1H), 7.31-7.48 (m, 2H), 7.52 (d, J=7.7 Hz, 1H).

$^{13}$C NMR δ (CDCl$_3$): 13.8, 22.1, 22.5, 26.6, 29.5, 30.0, 30.5, 39.1, 49.2, 54.5, 119.5, 126.7, 127.6, 127.7, 128.5, 128.8, 129.0, 135.6, 136.6, 137.0, 142.3, 148.6.

IR ν (neat, cm$^{-1}$): 3283, 3056, 2958, 2871, 1490 1464, 1428, 1314.

MS (ESI) m/z: 488 (M+H)$^+$.

Anal. Calcd. for C$_{26}$H$_{37}$N$_3$O$_2$S$_2$: C, 64.03; H, 7.65; N, 8.62. Found: C, 63.87; H, 7.80; N, 8.43.

(c) N-Butyloxycarbonyl-3-[3-(2-butylimidazol-1-ylmethyl)phenyl]-5-iso-butyl-thioiphene-2-sulfonamide To a solution of 3-[3-(2-butylimidazol-1-ylmethyl)phenyl]-5-iso-butyl-N-tert-butylthiophene-2-sulfonamide (18.4 mg, 0.038 mmol; see step (b)) in CH$_2$Cl$_2$ (1 mL) was added BCl$_3$ (0.25 mL, 1.0 M in hexane) and the reaction mixture was stirred for 1 h at ambient temperature. The reaction mixture was concentrated in vacuo. Water (5 mL) was added to the residue and this was then extracted with EtOAc. The combined organic phase was washed with water and brine, dried (over anhydrous MgSO$_4$) and concentrated in vacuo. To the crude product dissolved in CH$_2$Cl$_2$ (5 mL) was added Na$_2$CO$_3$ (18.0 mg, 0.17 mmol), water (2 mL) and butyl chloroformate (5.8 μL, 0.045 mmol) and the reaction mixture was stirred for 2 h at ambient temperature. The reaction mixture was diluted with CH$_2$Cl$_2$ (30 mL) and washed with citric acid (10% aq), brine and water, dried (over anhydrous MgSO$_4$), concentrated in vacuo, and the residue was purified by flash chromatography using MeOH:CH$_2$Cl$_2$ (7:93) as eluent to give the title compound as a white solid in 72% yield, over two steps, (14.5 mg, 0.027 mmol).

$^1$H NMR δ (CDCl$_3$): 0.70-0.91 (m, 6H), 0.96 (d, J=6.6 Hz, 6H), 1.14-1.42 (m, 4H), 1.44-1.56 (m, 2H), 1.57-1.71 (m, 2H), 1.82-1.98 (m, 1H), 2.65 (d, J=7.1 Hz), 2.87 (t, J=7.7 Hz, 2H), 3.98 (t, J=7.0 Hz), 5.01 (s, 2H), 6.66 (s, 1H), 6.71 s, 1H), 6.93 (s, 1H), 6.98 (d, J=7.6 Hz), 7.24 (apparent t, J=7.6 Hz, 1H), 7.45 (d, J=7.5 Hz), 7.58 (s, 1H), 8.61 (br s, 1H).

$^{13}$C NMR δ (CDCl$_3$): 13.7, 13.8, 19.0, 22.3, 24.9, 30.1, 30.5, 30.9, 39.2, 50.3, 65.2, 120.3, 121.8, 126.6, 128.3, 128.5, 129.5, 129.9, 133.4, 136.7, 137.0, 141.8, 147.3, 147.9, 156.3.

IR ν (neat, cm$^{-1}$): 3138, 3054, 2958, 2871, 1663, 1608, 1464, 1272.

MS (ESI) m/z: 532 (M+H)$^+$.

Anal. Calcd. for C$_{27}$H$_{37}$N$_3$O$_4$S$_2$: C, 60.99; H, 7.01; N, 7.90. Found: C, 60.91; H, 6.95; N, 7.80.

EXAMPLE 7

N-Butyloxycarbonyl-3-[3-(3-trifluoromethylpyrazol-1-ylmethyl)phenyl]-5-iso-butylthiophene-2-sulfonamide

(a) 3-[3-(3-Trifluoromethylpyrazol-1-ylmethyl)phenyl]-5-iso-butyl-N-tert-butyl-thiophene-2-sulfonamide To a pre-stirred (for 40 minutes at ambient temperature) solution of 2-trifluoromethylpyrazole (116.8 mg, 0.858 mmol) in DMSO (1 mL) and t-BuOK (40.5 mg, 0.361 mmol), was added a solution of 3-(3-bromomethylphenyl)-5-iso-butyl-N-tert-butylthiophene-2-sulfonamide (76.3 mg, 0.172 mmol; see Example 1(e)) in DMSO (1 mL) dropwise. The reaction mixture was stirred for 1 h at ambient temperature and then diluted with CH$_2$Cl$_2$ (15 mL). The organic layer was washed with water, dried (over anhydrous MgSO$_4$), concentrated in vacuo, and the residue purified by flash chromatography using EtOAc:petroleum ether (15:85) as eluent and LCMS (40-100% CH$_3$CN in water) to give the sub-title compound in 55% yield as a colourless syrup (47 mg, 0.095 mmol).

$^1$H NMR δ (CDCl$_3$): 0.90 (s, 9H), 0.96 (d, J=6.6 Hz, 6H), 1.85-2.00 (m, 1H), 2.67 (d, J=7.1 Hz, 2H), 4.12 (s, 1H), 5.36 (s, 2H), 6.55 (d, J=2.1 Hz, 1H), 6.75 (s, 1H), 7.32 (m, 1H), 7.44 (apparent t, J=7.7 Hz, 1H), 7.50-7.58 (m, 2H), 7.62 (m, 1H).

$^{13}$C NMR δ (CDCl$_3$): 22.1, 29.3, 30.5, 39.1, 54.4, 56.4, 104.9, 121.2 (q, J=267.0 Hz, CF$_3$), 128.0, 128.5, 129.0, 129.1, 131.1, 135.59, 135.61, 136.9, 142.1 (q, J=38.3 Hz, C—CF$_3$), 143.0, 148.5.

IR ν (neat, cm$^{-1}$): 3295, 3125, 2961, 2934, 1491, 1320.

MS (ESI) m/z: 500 (M+H)$^+$.

Anal. Calcd. for C$_{23}$H$_{28}$F$_3$N$_3$O$_2$S$_2$: C, 55.29; H, 5.65; N, 8.41. Found: C, 55.38; H, 5.83; N, 8.26.

(b) N-Butyloxycarbonyl-3-[3-(3-trifluoromethylpyrazol-1-ylmethyl)phenyl]-5-iso-butylthiophene-2-sulfonamide To a solution of 3-[3-(3-trifluoromethylpyrazol-1-ylmethyl)phenyl]-5-iso-butyl-N-tert-butylthiophene-2-sulfonamide (43.5 mg, 0.087 mmol; see step (a)) in CH$_2$Cl$_2$ (2 mL) was added BCl$_3$ (0.6 mL, 1.0 M in hexane) and the reaction mixture was stirred for 1 h at ambient temperature. The reaction mixture was concentrated in vacuo. Water (5 mL) was added to the residue and this was then extracted with EtOAc. The combined organic phase was washed with water and brine, dried (over anhydrous MgSO$_4$) and concentrated in vacuo. To the crude product dissolved in pyridine (1.5 mL) was added pyrrolidinopyridine (25.8 mg, 0.174 mmol) and butyl chloroformate (110.7 μL, 0.87 mmol) and the reaction mixture was stirred overnight. Citric acid (3 mL, 10% aq) was added to the reaction mixture, which was then extracted with EtOAc, dried (over anhydrous MgSO$_4$), concentrated in vacuo, and the residue purified by LCMS (40-100% CH$_3$CN in water) to give the title compound in 88% yield, over two steps, (41.6 mg, 0.076 mmol).

$^1$H NMR δ (CDCl$_3$): 0.83 (t, J=7.2 Hz, 3H), 0.99 (d, J=6.6 Hz, 6H), 1.05-1.25 (m, 2H), 1.35-1.50 (m, 2H), 1.85-2.05 (m, 1H), 2.71 (d, J=6.9 Hz, 2H), 3.95 (t, J=6.6 Hz, 2H), 5.34 (s, 2H), 6.54 (d, J=2.3 Hz, 1H), 6.80 (s, 1H), 7.26-7.34 (m, 1H), 7.34-7.46 (m, 2H), 7.54 (d, J=1.3 Hz, 1H), 7.62 (s, 1H), 8.08 (br s, 1H).

$^{13}$C NMR δ (CDCl$_3$): 13.5, 18.6, 22.2, 30.3, 30.5, 39.3, 56.4, 66.6, 104.7, 121.1 (q, J=269.6 Hz, CF$_3$), 128.4, 128.6, 128.7, 129.1, 129.6, 131.2, 131.5, 134.6, 134.9, 143.1 (q, J=37.8 Hz, C—CF$_3$), 145.0, 150.1, 151.5.

IR ν (neat, cm$^{-1}$): 3219, 3128, 2961, 2934, 2873, 1751, 1718, 1491, 1449, 1345.

MS (ESI) m/z: 544 (M+H)$^+$.

Anal. Calcd. for C$_{24}$H$_{28}$F$_3$N$_3$O$_4$S$_2$: C, 53.03; H, 5.19; N, 7.73. Found: C, 53.07; H, 5.35; N, 7.62.

EXAMPLE 8

N-Butyloxycarbonyl-3-(3-imidazo[4,5-b]pyridin-3-ylmethylphenyl)-5-iso-butylthiophene-2-sulfonamide (a) 3-(3-Imidazo[4,5-b]pyridin-3-ylmethylphenyl)-5-iso-butyl-N-tert-butylthiophene-2-sulfonamide; and (b) 3-(3-Imidazo[4,5]pyridin-1-ylmethylphenyl)-5-iso-butyl-N-tert-butylthiophene-2-sulfonamide To a solution of azobenzimidazole (20.6 mg, 0.173 mmol) in DMSO (1 mL) and KOH (18.5 mg, 0.331 mmol), that had been stirred for 40 min at ambient temperature, was added a solution of 3-(3-bromomethylphenyl)-5-iso-butyl-N-tert-butylthiophene-2-sulfonamide (70.0 mg, 0.158 mmol; see Example 1(e)) in DMSO (1 mL) dropwise. The reaction mixture was stirred for 1 h at ambient temperature and then diluted with CH$_2$Cl$_2$ (15 mL). The organic layer was washed with water, dried (over anhydrous MgSO$_4$), concentrated in vacuo, and the residue purified by flash chromatography using MeOH:CH$_2$Cl$_2$ (5:95 to 6:94) as eluent to give the two sub-title compounds (a) and (b) in 49% (Example 8(a), 37.2 mg, 0.077 mmol) and 19% (Example 8(b), 14.8 mg, 0.030 mmol) yield.

EXAMPLE 8(a)

$^1$H NMR δ (CDCl$_3$): 0.83 (s, 9H), 0.95 (d, J=6.6 Hz, 6H), 1.81-2.00 (m, 1H), 2.65 (d, J=7.1 Hz, 2H), 4.69 (brs, 1H), 5.48 (s, 2H), 6.73 (s, 1H), 7.25 (ddd, J=7.9, 4.8, 1.0 Hz, 1H), 7.29-7.43 (m, 2H), 7.47 (d, J=7.1 Hz, 1H), 7.76 (s, 1H), 8.07 (apparent d, J=7.9 Hz, 1H), 8.16 (s, 1H), 8.41 (m, 1H).

$^{13}$C NMR δ (CDCl$_3$): 22.1, 29.3, 30.5, 39.1, 47.4, 54.2, 118.5, 127.5, 128.2, 128.5, 128.6, 128.98, 129.01, 135.54, 135.57, 136.1, 137.1, 142.1, 143.9, 144.5, 146.8, 148.3.

IR ν (neat, cm$^{-1}$): 3278, 3093, 3057, 2960, 2926, 2870, 1600, 1498, 1410, 1318.

MS (ESI) m/z: 483 (M+H)$^+$.

Anal. Calcd. for C$_{25}$H$_{30}$N$_4$O$_2$S$_2$: C, 62.21; H, 6.26; N, 11.61. Found: C, 62.05; H, 6.45; N, 11.41.

EXAMPLE 8(b)

$^1$H NMR δ (CDCl$_3$): 0.91 (s, 9H), 0.96 (d, J=6.6 Hz, 6H), 1.80-2.00 (m, 1H), 2.66 (d, J=7.1 Hz, 2H), 4.04 (br s, 1H), 5.40 (s, 2H), 6.69 (s, 1H), 7.14-7.24 (m, 2H), 7.40 (apparent t, J=7.7 Hz, 1H), 7.52 (d, J=7.7 Hz, 1H), 7.58 (br s, 1H), 7.66-7.76 (m, 1H), 8.25 (s, 1H), 8.52-8.62 (m, 1H).

$^{13}$C NMR δ (CDCl$_3$): 22.1, 29.5, 30.5, 39.1, 49.4, 54.6, 118.3, 118.4, 125.9, 127.2, 128.4, 128.8, 129.18, 129.24, 135.1, 135.8, 135.7, 142.2, 145.2, 148.8, 156.5.

IR (cm$^{-1}$): 3077, 3053, 2959, 2928, 2870, 1610, 1493, 1315. MS (ESI) m/z: 483 (M+H)$^+$.

Anal. Calcd. for C$_{25}$H$_{30}$N$_4$O$_2$S$_2$: C, 62.21; H, 6.26; N, 11.61. Found: C, 62.36; H, 6.39; N, 11.73.

(c) N-Butyloxycarbonyl-3-(3-imidazo[4,5-b]pyridin-3-ylmethylphenyl)-5-iso-butylthiophene-2-sulfonamide To a solution of 3-(3-imidazo[4,5-b]pyridin-3-ylmethylphenyl)-5-iso-butyl-N-tert-butylthiophene-2-sulfonamide (53.6 mg, 0.111 mmol; see Example 8(a)) in CH$_2$Cl$_2$ (2 mL) was added BCl$_3$ (0.6 mL, 1.0 M in hexane) and the reaction mixture was stirred for 1 h at ambient temperature. The reaction mixture was concentrated in vacuo. Water (5 mL) was added to the residue and this was then extracted with EtOAc. The combined organic phase was washed with water and brine, dried (over anhydrous MgSO$_4$) and concentrated in vacuo. To the crude product dissolved in pyridine (1.5 mL) was added pyrrolidinopyridine (32.9 mg, 0.222 mmol) and butyl chloroformate (141.3 μL, 1.11 mmol) and the reaction mixture was stirred overnight. Citric acid (3 mL, 10% aq) was added to the reaction mixture, which was then extracted with EtOAc, dried (over anhydrous MgSO$_4$), concentrated in vacuo, and the residue purified by LCMS (20-100% CH$_3$CN in water) to give the title compound in 70% yield, over two steps, (41 mg, 0.078 mmol).

$^1$H NMR δ (CDCl$_3$): 0.75 (t, J=7.3 Hz, 3H), 0.99 (d, J=6.6 Hz, 6H), 1.02-1.14 (m, 2H), 1.30-1.43 (m, 2H), 1.85-2.04 (m, 1H), 2.71 (d, J=6.9 Hz, 2H), 3.94 (t, J=6.5 Hz, 2H), 5.34 (s, 2H), 6.81 (s, 1H), 7.10-7.33 (m, 4H), 7.87 (s, 1H), 8.07 (d, J=7.9 Hz, 1H), 8.14 (s, 1H), 8.37 (dd, J=4.9, 1.3 Hz, 1H).

$^{13}$C NMR δ (CDCl$_3$): 13.5, 18.6, 22.2, 30.3, 30.5, 39.3, 48.2, 66.3, 118.5, 127.5, 128.2, 128.4, 128.6, 129.1, 129.9, 132.3, 134.7, 135.2, 135.7, 144.2, 144.3, 144.7, 146.1, 151.1.

IR ν (neat, cm$^{-1}$): 3057, 2959, 2871, 1740, 1600, 1502, 1465, 1411, 1344.

MS (ESI) m/z: 527 (M+H)$^+$.

Anal. Calcd. for C$_{26}$H$_{30}$N$_4$O$_4$S$_2$: C, 59.29; H, 5.74; N, 10.64. Found: C, 59.16; H, 5.83; N, 10.48.

EXAMPLE 9

N-Butyloxycarbonyl-3-(3-imidazo[4,5-b]pyridin-1-ylmethylphenyl)-5-iso-butyl-thiophene-2-sulfonamide To a solution of 3-(3-imidazo[4,5-b]pyridin-1-ylmethylphenyl)-5-iso-butyl-N-tert-butylthiophene-2-sulfonamide (35.7 mg, 0.074 mmol; see Example 8(b)) in CH$_2$Cl$_2$ (2 mL) was added BCl$_3$ (0.6 mL, 1.0 M in hexane) and the reaction mixture was stirred for 1 h at ambient temperature. The reaction mixture was concentrated in vacuo. Water (5 mL) was added to the residue and this was then extracted with EtOAc. The combined organic phase was washed with water and brine, dried (over anhydrous MgSO$_4$) and concentrated in vacuo. To the crude product dissolved in pyridine (1.5 mL) was added pyrrolidinopyridine (21.9 mg, 0.148 mmol) and butyl chloroformate (94.1 μL, 0.74 mmol) and the reaction mixture was stirred overnight. Citric acid (3 mL, 10% aq) was added to the reaction mixture, which was then extracted with EtOAc, dried (over anhydrous MgSO$_4$), concentrated in vacuo, and the residue purified by flash chromatography using MeOH:CH$_2$Cl$_2$ (5:95) as eluent to give the title compound in 58% yield, over two steps, (22.8 mg, 0.043 mmol).

$^1$H NMR δ (CDCl$_3$): 0.82 (t, J=7.3 Hz, 3H), 0.97 (d, J=6.6 Hz, 6H), 1.14-1.32 (m, 2H), 1.40-1.56 (m, 2H), 1.84-2.00 (m, 1H), 2.67 (d, J=7.1 Hz, 2H), 4.01 (t, J=6.5 Hz, 2H), 5.17 (s, 2H), 6.70 (s, 1H), 6.97 (d, J=7.7 Hz, 1H), 7.07 (dd, J=8.1, 4.8

Hz, 1H), 7.21 (apparent t, J=7.7 Hz, 1H), 7.37 (d, J=7.7 Hz, 1H), 7.54 (d, J=8.1 Hz, 1H), 7.56 (s, 1H), 8.03 (s, 1H), 8.36-8.46 (m, 1H).

$^{13}$C NMR δ (CDCl$_3$): 13.6, 18.8, 22.3, 30.46, 30.50, 39.2, 49.2, 66.6, 118.2, 118.9, 126.0, 126.9, 128.9, 129.0, 132.4, 134.4, 135.3, 144.9, 145.7, 150.9, 152.0, 155.6

IR ν (neat, cm$^{-1}$): 3052, 2959, 2871, 1740, 1611, 1493, 1347.

MS (ESI) m/z: 527 (M+H)$^+$.

Anal. Calcd. for C$_{26}$H$_{30}$N$_4$O$_4$S$_2$.×½H$_2$O: C, 58.30; H, 5.83; N, 10.46. Found: C, 58.46; H, 5.73; N, 10.81.

EXAMPLE 10

N-Butyloxycarbonyl-3-[3-(2-acetylimidazol-1-ylmethyl)phenyl]-5-iso-butylthio-phene-2-sulfonamide (a) 1-(1H-Imidazol-2-yl)ethanone The title compound was made prepared in accordance with a literature method (*Journal of Organic Chemistry* 1980, 45, 4038-4040).

$^1$H NMR δ (CDCl$_3$): 2.67 (s, 3H), 7.28 (s, 2H), 11.70 (br s, 1H).

$^{13}$C NMR δ (CDCl$_3$): 190.0, 145.3, 131.3, 120.7, 25.6; IR (CM$^{-1}$): 1672.

(b) 3-[3-(2-Acetylimidazol-1-ylmethyl)phenyl]-5-iso-butyl-N-tert-butylthiophene-2-sulfonamide To a solution of 2-acetoimidazole (59.5 mg, 0.54 mmol; see step (a)) in DMSO (1 mL) and NaOH (15.1 mg, 0.378 mmol), that had been stirred for 40 min at ambient temperature, was added a solution of 3-(3-bromomethylphenyl)-5-iso-butyl-N-tert-butylthiophene-2-sulfonamide (80 mg, 0.18 mmol; see Example 1(e)) in DMSO (1 mL) dropwise. The reaction mixture was stirred for 1 h at ambient temperature and then diluted with CH$_2$Cl$_2$ (15 mL). The organic layer was washed with water, dried (over anhydrous MgSO$_4$), concentrated in vacuo, and the residue purified by flash chromatography using MeOH:CH$_2$Cl$_2$ (3:97) as eluent to give the sub-title compound in 96% yield as a colourless syrup (81.0 mg, 0.171 mmol).

$^1$H NMR δ (CDCl$_3$): 0.92 (s, 9H), 0.96 (d, J=6.6 Hz), 1.80-2.00 (m, 1H), 2.55-2.75 (m, 5H), 4.74 (s, 1H), 5.61 (s, 2H), 6.75 (s, 1H), 7.02-7.13 (m, 1H), 7.23 (s, 1H), 7.24 (s, 1H), 7.30-7.43 (m, 2H), 7.67 (s, 1H).

$^{13}$C NMR δ (CDCl$_3$): 22.1, 27.3, 29.4, 30.5, 39.1, 51.9, 54.1, 126.3, 126.7, 128.0, 128.2, 128.5, 128.7, 129.7, 135.3, 136.9, 137.0, 142.0, 142.6, 148.2, 190.8.

IR ν (neat, cm$^{-1}$): 3304, 3106, 2961, 2870, 1672, 1464, 1408, 1320.

MS (ESI) m/z: 474 (M+H)$^+$.

Anal. Calcd. for C$_{24}$H$_{31}$N$_3$O$_3$S$_2$: C, 60.86; H, 6.60; N, 8.87. Found: C, 60.87; H, 6.59; N, 8.77.

(c) N-Butyloxycarbonyl-3-[3-(2-acetylimidazol-1-ylmethyl)phenyl]-5-iso-butyl-thiophene-2-sulfonamide To a solution of 3-[3-(2-acetylimidazol-1-ylmethyl)phenyl]-5-iso-butyl-N-tert-butylthiophene-2-sulfonamide (62.4 mg, 0.132 mmol; see step (b)) in TFA (2 mL) was added anisole (150 μL) and the reaction mixture was stirred overnight at ambient temperature. The reaction mixture was concentrated in vacuo and dried in vacuo overnight. To the crude product dissolved in CH$_2$Cl$_2$ (2 mL) was added Na$_2$CO$_3$ (302 mg, 2.85 mmol), water (0.8 mL) and butyl chloroformate (83.8 μL, 0.659 mmol) and the reaction mixture was stirred overnight at ambient temperature. The reaction mixture was diluted with CH$_2$Cl$_2$ (30 mL) and washed with citric acid (10% aq), brine and water, dried (over anhydrous MgSO$_4$), concentrated in vacuo, and the residue purified by flash chromatography using MeOH:CH$_2$Cl$_2$ (5:95) as eluent to give the title compound as a white solid in 34% yield, over two steps, (23 mg, 0.0045 nmol).

$^1$H NMR δ (CDCl$_3$): 0.82 (t, J=7.2 Hz, 3H), 0.99 (d, J=6.6 Hz, 6H), 1.08-1.22 (m, 2H), 1.36-1.50 (m, 2H), 1.86-2.02 (m, 1H), 2.60 (s, 3H), 2.70 (d, J=6.9 Hz, 2H), 3.96 (t, J=6.5 Hz, 2H), 5.52 (s, 2H), 6.80 (s, 1H), 6.90-6.98 (m, 1H), 7.18-7.36 (m, 4H), 7.77-7.83 (m, 1H), 9.54 (br s, 1H).

$^{13}$C NMR δ (CDCl$_3$): 13.6, 18.7, 22.2, 26.9, 30.4, 30.5, 39.3, 52.5, 66.3, 126.3, 127.4, 127.8, 128.7, 128.8, 129.4, 129.8, 131.6, 134.3, 136.6, 142.5, 144.4, 150.5, 151.1, 191.9.

IR ν (neat, cm$^{-1}$): 3118, 2960, 2871, 1748, 1665, 1464, 1408, 1346.

MS (ESI) m/z: 518 (M+H)$^+$.

Anal. Calcd. for C$_{25}$H$_{31}$N$_3$O$_5$S$_2$: C, 58.00; H, 6.04; N, 8.12. Found: C, 57.82; H, 6.11; N, 7.95.

EXAMPLE 11

N-Butyloxycarbonyl-3-[3-(2-chloroimidazol-1-ylmethyl)phenyl]-5-iso-butylthio-phene-2-sulfonamide (a) 2-Bromo-1H-imidazole The title compound was made prepared in accordance with a literature method (*Journal of Organic Chemistry* 1978, 43, 381-4833).

$^1$H NMR δ (15% CD$_3$OD in CDCl$_3$) 6.91 (s, 1H), 6.92 (s, 1H).

$^{13}$C NMR δ (15% CD$_3$OD in CDCl$_3$): 116.5, 124.7.

(b) 3-[3-(2-Bromoimidazol-1-ylmethyl)phenyl]-5-iso-butyl-N-tert-butylthiophene-2-sulfonamide To a solution of 2-bromoimidazole (68.9 mg, 0.469 mmol; see step (a)) in DMSO (1 mL) and NaOH (32.8 mg, 0.82 mmol), that had been stirred for 40 min at ambient temperature, was added a solution of 3-(3-bromomethylphenyl)-5-iso-butyl-N-tert-butylthiophene-2-sulfonamide (173.6 mg, 0.391 mmol; see Example 1(e)) in DMSO (1 mL) dropwise. The reaction mixture was stirred for 1 h at ambient temperature and then diluted with CH$_2$Cl$_2$ (15 mL). The organic layer was washed with water, dried (over anhydrous MgSO$_4$), concentrated in vacuo, and the residue purified by flash chromatography using MeOH:CH$_2$Cl$_2$ (3:97) as eluent to give the sub-title compound in 99% yield as a colourless syrup (197.3 mg, 0.387 mmol).

$^1$H NMR δ (CDCl$_3$): 0.94 (s, 9H), 0.96 (d, J=6.8 Hz, 6H), 1.82-2.00 (m, 1H), 2.67 (d, J=7.1 Hz, 2H), 4.03 (br s, 1H), 5.14 (s, 2H), 6.73 (s, 1H), 7.05 (s, 1H), 7.08 (s, 1H), 7.22 (d, J=7.6 Hz, 1H), 7.42 (apparent t, J=7.6 Hz, 1H), 7.45-7.57 (m, 2H).

$^{13}$C NMR δ (CDCl$_3$): 22.1, 29.5, 30.5, 39.1, 51.1, 54.5, 119.6, 122.3, 127.4, 128.2, 128.7, 128.9, 129.1, 130.4, 135.7, 135.9, 136.7, 142.2, 148.6.

IR ν (neat, cm$^{-1}$): 3287, 3113, 2961, 2870, 1465, 1433, 1387, 1318.

MS (ESI) m/z: 510 (M+H)$^+$, 512 (M+H)$^+$+2.

Anal. Calcd. for C$_{22}$H$_{28}$BrN$_3$O$_2$S$_2$: C, 51.76; H, 5.53; N, 8.23. Found: C, 51.68; H, 5.61; N, 8.08.

(c) N-Butyloxycarbonyl-3-[3-(2-chloroimidazol-1-ylmethyl)phenyl]-5-iso-butyl-thiophene-2-sulfonamide To a solution of 3-[3-(2-bromoimidazol-1-ylmethyl)phenyl]-5-iso-butyl-N-tert-butylthiophene-2-sulfonamide (44.1 mg, 0.086 mmol; see step (b)) in TFA (3 mL) was added anisole (150 µL) and the reaction mixture was stirred overnight at ambient temperature. The reaction mixture was concentrated in vacuo and dried in vacuo overnight. To the crude product dissolved in pyridine (1.5 mL) was added pyrrolidinopyridine (25.6 mg, 0.173 mmol) and butyl chloroformate (109.9 µL, 0.846 mmol) and the reaction mixture was stirred for 36 h. Citric acid (3 mL, 10% aq) was added to the reaction mixture, which was then extracted with EtOAc, dried (over anhydrous $MgSO_4$), concentrated in vacuo, and the residue purified by flash chromatography using $MeOH:CH_2Cl_2$ (5:95) as eluent to give the title compound in 57% yield, over two steps, (25 mg, 0.049 mmol).
$^1$H NMR δ ($CDCl_3$): 0.87 (t, J=7.3 Hz, 3H), 0.99 (d, J=6.6 Hz, 6H), 1.15-1.33 (m, 2H), 1.45-1.60 (m, 2H), 1.85-2.02 (m, 1H), 2.70 (d, J=7.1 Hz, 2H), 4.04 (t, J=6.6 Hz, 2H), 5.08 (s, 2H), 6.73 (s, 1H), 6.87 (d, J=1.5 Hz, 1H), 6.90 (d, J=1.5 Hz, 1H), 7.14 (m, 1H), 7.27-7.45 (m, 3H).
$^{13}$C NMR δ ($CDCl_3$): 13.6, 18.7, 22.2, 30.4, 30.5, 39.2, 49.9, 66.8, 121.2, 127.4, 128.2, 128.4, 128.9, 129.2, 131.4, 131.9, 134.9, 135.3, 145.4, 150.7, 151.5.
MS (ESI) m/z: 512 (M+H)$^+$+2, 510 (M+H)$^+$.
IR ν (neat, cm$^{-1}$): 3126, 3043, 2959, 2871, 1740, 1608, 1587, 1474, 1389, 1344.
Anal. Calcd. for $C_{23}H_{28}ClN_3O_4S_2$: C, 54.16; H, 5.53; N, 8.24. Found: C, 53.88; H, 5.70; N, 8.12.

EXAMPLE 12

N-Butyloxycarbonyl-3-[3-(2-yl-pyridin-2-ylimidazol-1-ylmethyl)-phenyl]-5-iso-butylthiophene-2-sulfonamide (a) 2-(1H-Imidazol-2-yl)-pyridine The title compound was prepared in accordance with a literature method (*Tetrahedron Lett.* 1988, 29(39), 5013-5016).

(b) 3-[3-(2-Pyridin-2-yl-imidazol-1-ylmethyl)phenyl]-5-iso-butyl-N-tert-butylthio-phene-2-sulfonamide To a solution of 2-(2'-pyridinyl)imidazole (32.9 mg, 0.227 mmol; see step (a)) in DMSO (1 mL) and NaOH (18.6 mg, 0.465 mmol), that had been stirred for 40 min at ambient temperature, was added a solution of 3-(3-bromomethylphenyl)-5-iso-butyl-N-tert-butylthiophene-2-sulfonamide (120.9 mg, 0.272 mmol; see Example 1(e)) in DMSO (1 mL) dropwise. The reaction mixture was stirred for 1 h at ambient temperature and then diluted with $CH_2Cl_2$ (15 mL). The organic layer was washed with water, dried (over anhydrous $MgSO_4$), concentrated in vacuo, and the residue purified by flash chromatography using $MeOH:CH_2Cl_2$ (3:97) as eluent to give the sub-title compound in 51% yield as a white solid (58.3 mg, 0.116 mmol).
$^1$H NMR δ ($CDCl_3$): 0.81 (s, 9H), 0.95 (d, J=6.6 Hz, 6H), 1.80-2.00 (m, 1H), 2.65 (d, J=7.1 Hz, 2H), 4.03 (br s, 1H), 5.97 (s, 2H), 6.69 (s, 1H), 7.10 (s, 1H), 7.14-7.26 (m, 3H), 7.34 (apparent t, J=7.6 Hz, 1H), 7.46 (d, J=7.6 Hz, 1H), 7.56 (s, 1H), 7.64-7.80 (m, 1H), 8.19 (d, J=8.1 Hz, 1H), 8.59 (d, J=4.3 Hz, 1H).
$^{13}$C NMR δ ($CDCl_3$): 22.1, 29.3, 30.5, 39.1, 51.2, 54.2, 122.6, 122.8, 123.5, 127.3, 128.1, 128.6, 128.8, 128.9, 135.3, 136.6, 136.7, 138.4, 142.4, 144.4, 148.3, 150.6.
IR ν (neat, cm$^{-1}$): 3290, 3108, 2959, 2870, 1589, 1567, 1488, 1460, 1321.
MS (ESI) m/z: 509 (M+H)$^+$.
Anal. Calcd. for $C_{27}H_{32}N_4O_2S_2$: C, 63.75; H, 6.34; N, 11.01. Found: C, 63.44; H, 6.44; N, 10.79.

(c) N-Butyloxycarbonyl-3-[3-(2-pyridin-2-ylimidazol-1-ylmethyl)phenyl]-5-iso-butylthiophene-2-sulfonamide To a solution of 3-[3-(2-pyridin-2-ylimidazol-1-ylmethyl)phenyl]-5-iso-butyl-N-tert-butylthiophene-2-sulfonamide (46.7 mg, 0.0918 mmol; see step (b)) in $CH_2Cl_2$ (1 mL) was added $BCl_3$ (0.18 mL, 1.0 M in hexane) and the reaction mixture was stirred for 1 h at ambient temperature. The reaction mixture was concentrated in vacuo. Water (5 mL) was added to the residue and this was then extracted with EtOAc. The combined organic phase was washed with water and brine, dried (over anhydrous $MgSO_4$) and concentrated in vacuo. To the crude product dissolved in $CH_2Cl_2$ (5 mL) was added $Na_2CO_3$ (43.8 mg, 0.413 mmol), water (2 mL) and butyl chloroformate (16.3 µL, 0.0129 mmol) and the reaction mixture was stirred for 23 h at ambient temperature. The reaction mixture was diluted with $CH_2Cl_2$ (30 mL) and washed with citric acid (10% aq), brine and water, dried (over anhydrous $MgSO_4$), concentrated in vacuo, and the residue purified by flash chromatography using $MeOH:CH_2Cl_2$ (6:94) as eluent to give the title compound as a white solid in 63% yield, over two steps, (32 mg, 0.058 mmol).
$^1$H NMR δ ($CDCl_3$): 0.82 (t, J=7.3 Hz, 3H), 0.97 (d, J=6.6 Hz, 6H), 1.05-1.22 (m, 2H), 1.30-1.50 (m, 2H), 1.82-2.00 (m, 1H), 2.68 (d, J=6.9 Hz, 2H), 3.94 (t, J=6.6 Hz, 2H), 5.74 (s, 2H), 5.89 (br s, 1H), 6.73 (s, 1H), 6.95 (s, 1H), 7.04 (s, 1H), 7.10-7.35 (m, 4H), 7.43 (s, 1H), 7.77 (m, 1H), 8.10 (d, J=8.1 Hz, 1H), 8.55 (d, J=4.1 Hz, 1H).
$^{13}$C NMR δ ($CDCl_3$): 13.6, 18.7, 22.2, 30.3, 30.5, 39.2, 50.9, 66.4, 123.0, 123.8, 127.2, 127.8, 127.9, 128.5, 128.8, 131.5, 134.5, 137.0, 137.7, 144.9, 145.2, 148.4, 150.0, 150.6, 151.1.
IR ν (neat, cm$^{-1}$): 3047, 2959, 2871, 1741, 1589, 1489, 1465, 1344, 1280, 1226.
MS (ESI) m/z: 553 (M+H)$^+$.
Anal. Calcd. for $C_{28}H_{32}N_4O_4S_2$: C, 60.85; H, 5.84; N, 10.14. Found: C, 60.72; H, 5.86; N, 10.20.

EXAMPLE 13

N-Butyloxycarbonyl-3-[3-(2-phenylimidazol-1-ylmethyl)phenyl]-5-iso-butyl-thiophene-2-sulfonamide (a) 3-[3-(2-Phenylimidazol-1-ylmethyl)phenyl]-5-iso-butyl-N-tert-butylthiophene-2-sulfonamide To a solution of 3-[3-(2-bromoimidazol-1-ylmethyl)phenyl]-5-iso-butyl-N-tert-butylthiophene-2-sulfonamide (58.5 mg, 0.115 mmol; see Example 11(b)) in toluene (5 mL) and ethanol (0.5 mL) was added phenyl boronic acid (55.9 mg, 0.458 mmol), $Pd(PPh_3)_4$ (7.9 mg, 6.88 µmol), NaOH (0.46 mL, 0.688 mmol, 1.5 M aq), and the reaction mixture was stirred for 4 h at 90° C. Another portion of phenyl boronic acid (20.0 mg, 0.164 mmol) and $Pd(PPh_3)_4$ (2.0 mg, 1.7 µmol)

were added and the reaction was stirred overnight at 90° C. The reaction mixture was diluted with EtOAc (30 mL) and washed with water, dried (over anhydrous MgSO$_4$), concentrated in vacuo, and the residue purified by flash chromatography using EtOAc:hexane (8:2) as eluent to give the sub-title compound in 49% yield (28.4 mg, 0.056 mmol).

$^1$H NMR δ (CDCl$_3$): 0.80-1.10 (m, 15H), 1.91 (m, 1H), 2.67 (d, J=7.1 Hz, 2H), 4.01 (br s, 1H), 5.27 (s, 2H), 6.69 (s, 1H), 6.97-7.07 (m, 2H), 7.19 (s, 1H), 7.32-7.46 (m 5H), 7.49-7.60 (m, 3H).

$^{13}$C NMR δ (CDCl$_3$): 22.1, 29.5, 30.5, 39.1, 50.3, 54.5, 121.2, 126.7, 127.6, 128.6, 128.8, 128.9, 129.06, 129.13, 130.4, 135.6, 136.6, 137.2, 142.4, 148.2, 148.6.

IR ν (neat, cm$^{-1}$): 3287, 3058, 2960, 2870, 1606, 1543, 1472, 1416, 1317.

MS (ESI) m/z: 508 (M+H)$^+$.

Anal. Calcd. for C$_{28}$H$_{33}$N$_3$O$_2$S$_2$×1½H$_2$O: C, 62.89; H, 6.79; N, 7.86. Found: C, 63.07; H, 6.56; N, 7.60.

(b) N-Butyloxycarbonyl-3-[3-(2-phenylimidazol-1-ylmethyl)phenyl]-5-iso-butyl-thiophene-2-sulfonamide To a solution of 3-[3-(2-phenylimidazol-1-ylmethyl)phenyl]-5-iso-butyl-N-tert-butylthiophene-2-sulfonamide (31.2 mg, 0.0615 mmol; see step (a)) in CH$_2$Cl$_2$ (1 mL) was added BCl$_3$ (0.2 mL, 1.0 M in hexane) and the reaction mixture was stirred for 1 h at ambient temperature. The reaction mixture was concentrated in vacuo. Water (5 mL) was added to the residue and this was then extracted with EtOAc. The combined organic phase was washed with water and brine, dried (over anhydrous MgSO$_4$) and concentrated in vacuo. To the crude product dissolved in CH$_2$Cl$_2$ (5 mL) was added Na$_2$CO$_3$ (29.3 mg, 0.277 mmol), water (2 mL) and butyl chloroformate (15.6 μL, 0.123 mmol), and the reaction mixture was stirred for 11 h at ambient temperature. The reaction mixture was diluted with CH$_2$Cl$_2$ (30 mL) and washed with citric acid (10% aq), brine and water, dried (over anhydrous MgSO$_4$), concentrated in vacuo, and the residue purified by flash chromatography using MeOH:CH$_2$Cl$_2$ (5:95) as eluent to give the title compound as a white solid in 87% yield, over two steps, (29.4 mg, 0.0533 mmol).

$^1$H NMR δ (CDCl$_3$): 0.82 (t, J=7.1 Hz, 3H), 0.98 (d, J=6.6 Hz, 6H), 1.10-1.28 (m, 2H), 1.32-1.48 (m, 2H), 1.82-2.00 (m, 1H), 2.67 (d, J=6.9 Hz, 2H), 3.93 (t, J=6.7 Hz, 2H), 5.12 (s, 2H), 6.68 (s, 1H), 6.92 (d, J=1.2 Hz, 1H), 6.95 (s, 1H), 6.99 (d, J=7.6 Hz, 1H), 7.30 (d, J=7.6 Hz, 1H), 7.34-7.43 (m, 5H), 7.44-7.56 (m, 2H), 8.46 (br s, 1H).

$^{13}$C NMR δ (CDCl$_3$): 13.6, 18.7, 22.2, 30.5, 39.2, 50.3, 66.2, 121.3, 126.7, 127.5, 128.2, 128.7, 129.0, 129.1, 129.3, 132.8, 135.2, 136.1, 144.6, 147.4, 150.5, 152.2.

IR ν (neat, cm$^{-1}$): 3117, 3059, 2958, 2870, 1741, 1662, 1610, 1490, 1466, 1343.

MS (ESI) m/z: 552 (M+H)$^+$.

Anal. Calcd. for C$_{29}$H$_{33}$N$_3$O$_4$S$_2$: C, 63.13; H, 6.03; N, 7.62. Found: C, 62.98; H, 6.11; N, 7.50.

EXAMPLE 14

N-Butyloxycarbonyl-3-[3-(2-thiophen-3-yl-imidazol-1-ylmethyl)-phenyl]-5-iso-butylthiophene-2-sulfonamide (a) 3-[3-(2-Thiophen-3-yl-imidazol-1-ylmethyl)-phenyl]-5-iso-butyl-N-tert-butyl-thiophene-2-sulfonamide To a solution of 3-[3-(2-bromoimidazol-1-ylmethyl)phenyl]-5-iso-butyl-N-tert-butylthiophene-2-sulfonamide (61.7 mg, 0.121 mmol; see Example 11((b)) in toluene (5 mL) and ethanol (0.5 mL) was added 3-thienyl boronic acid (77.3 mg, 0.604 mmol), Pd(PPh$_3$)$_4$ (8.4 mg, 7.25 μmol) and NaOH (0.48 mL, 0.725 mmol, 1.5 M aq), and the reaction mixture stirred for 4 h at 90° C. Another portion of 3-thienyl boronic acid (60.0 mg, 0.469 mmol) and Pd(PPh$_3$)$_4$ (5.0 mg, 4.3 μmol) was added and the reaction was stirred overnight at 90° C. The reaction mixture was diluted with EtOAc (30 mL) and washed with water, dried (over anhydrous MgSO$_4$), concentrated in vacuo, and the residue purified by flash chromatography using EtOAc:hexane (8:2 to 9:1) as eluent to give the sub-title compound in 71% yield (44.3 mg, 0.0862 mmol).

$^1$H NMR δ (CDCl$_3$): 0.95 (d, J=6.4 Hz, 6H), 0.96 (s, 9H), 1.82-2.00 (m, 1H), 2.65 (d, J=6.9 Hz, 2H), 4.08 (br s, 1H), 5.32 (s, 2H), 6.69 (s, 1H), 6.97 (s, 1H), 7.05 (d, J=7.7 Hz, 1H), 7.16 (s, 1H), 7.30-7.46 (m, 5H), 7.52 (d, J=7.7 Hz, 1H).

$^{13}$C NMR δ (CDCl$_3$): 22.1, 29.5, 30.5, 39.1, 50.2, 54.6, 121.2, 124.1, 126.1, 126.4, 127.3, 127.9, 128.6, 128.8, 128.9, 129.1, 131.1, 135.7, 136.6, 137.0, 142.4, 143.9, 148.6.

IR ν (neat, cm$^{-1}$): 3276, 3107, 2960, 2869, 1464, 1439, 1388, 1315.

MS (ESI) m/z: 514 (M+H)$^+$.

Anal. Calcd. for C$_{26}$H$_{31}$N$_3$O$_2$S$_3$: C, 60.79; H, 6.08; N, 8.18. Found: C, 60.41; H, 6.04; N, 7.95.

(b) N-Butyloxycarbonyl-3-[3-(2-thiophen-3-yl-imidazol-1-ylmethyl)-phenyl]-5-iso-butylthiophene-2-sulfonamide To a solution of 3-[3-(2-thiophen-3-yl-imidazol-1-ylmethyl)-phenyl]-5-iso-butyl-N-tert-butylthiophene-2-sulfonamide (38.2 mg, 0.0744 mmol; see step (a)) in CH$_2$Cl$_2$ (1 mL) was added BCl$_3$ (0.2 mL, 1.0 M in hexane) and the reaction mixture was stirred for 1 h at ambient temperature. The reaction mixture was concentrated in vacuo. Water (5 mL) was added to the residue and this was then extracted with EtOAc. The combined organic phase was washed with water and brine, dried (over anhydrous MgSO$_4$) and concentrated in vacuo. To the crude product dissolved in CH$_2$Cl$_2$ (5 mL) was added Na$_2$CO$_3$ (35.5 mg, 0.335 mmol), water (2 mL) and butyl chloroformate (11.4 μL, 0.0893 mmol) and the reaction mixture was stirred for 5 h at ambient temperature. The reaction mixture was diluted with CH$_2$Cl$_2$ (30 mL) and washed with citric acid (10% aq), brine and water, dried (over anhydrous MgSO$_4$), concentrated in vacuo, and the residue purified by flash chromatography using MeOH:CH$_2$Cl$_2$ (5:95) as eluent to give the title compound as a white solid in 67% yield, over two steps, (28 mg, 0.050 mmol).

$^1$H NMR δ (CDCl$_3$): 0.82 (t, J=7.2 Hz, 3H), 0.96 (d, J=6.6 Hz, 6H), 1.10-1.30 (m, 2H), 1.35-1.60 (m, 2H), 1.80-2.00 (m, 1H), 2.65 (d, J=6.9 Hz, 2H), 3.91 (t, J=5.5 Hz, 2H), 5.19 (s, 2H), 6.69 (s, 1H), 6.92 (s, 1H), 6.94-7.04 (m 2H), 7.27-7.35 (m, 4H), 7.35-7.44 (m, 2H), 7.44-7.50 (m, 1H).

$^{13}$C NMR δ (CDCl$_3$): 13.7, 18.8, 22.3, 30.47, 30.56, 39.2, 50.3, 66.4, 121.4, 125.6, 126.2, 126.3, 127.2, 127.9, 128.0, 128.7, 128.8, 128.9, 129.4, 133.6, 135.5, 136.0, 143.3, 143.9, 149.7.

IR ν (neat, cm$^{-1}$): 3102, 2957, 2870, 1740, 1639, 1607, 1464, 1280.

MS (ESI) m/z: 558 (M+H)$^+$.

Anal. Calcd. for C$_{27}$H$_{31}$N$_3$O$_4$S$_3$: C, 56.92; H, 5.72; N, 7.38. Found: C, 56.76; H, 5.74; N, 7.28.

EXAMPLE 15

N-Butyloxycarbonyl-3-[3-(2-thiophen-2-yl-imidazol-1-ylmethyl)phenyl]-5-iso butylthiophene-2-sulfonamide (a) 3-[3-(2-Thiophen-2-yl-imidazol-1-ylmethyl)phenyl]-5-iso-butyl-N-tert-butyl-thiophene-2-sulfonamide To a solution of 3-[3-(2-bromoimidazol-1-ylmethyl)phenyl]-5-iso-butyl-N-tert-butylthiophene-2-sulfonamide (22 mg, 0.0431 mmol; see example 11 (b)) in toluene (5 mL) and ethanol (0.5 mL) was added 2-thienyl boronic acid (27.6 mg, 0.216 mmol), Pd(PPh$_3$)$_4$ (3.0 mg, 2.59 µmol) and NaOH (0.17 mL, 0.26 mmol, 1.5 M aq), and the reaction mixture stirred for 4 h at 90° C. Another portion of 2-thienyl boronic acid (27.6 mg, 0.216 mmol) and Pd(PPh$_3$)$_4$ (3.0 mg, 2.6 mmol) was added and the reaction was stirred overnight at 90° C. The reaction mixture was diluted with EtOAc (30 mL) and washed with water, dried (over anhydrous MgSO$_4$), concentrated in vacuo, and the residue purified by flash chromatography using EtOAc:hexane (7:3) as eluent to give the sub-title compound in 90% yield (20 mg, 0.039 mmol).

$^1$H NMR δ (CDCl$_3$): 0.95 (s, 9H), 0.96 (d, J=6.5 Hz, 9H), 1.82-2.00 (m, 1H), 2.67 (d, J=6.9 Hz, 2H), 3.98 (br s, 1H), 5.39 (s, 2H), 6.69 (s, 1H), 6.97-7.11 (m, 3H), 7.12-7.21 (m, 2H), 7.31-7.45 (m, 3H), 7.52 (d, J=7.7 Hz, 1H).

$^{13}$C NMR δ (CDCl$_3$): 22.1, 29.5, 30.5, 39.1, 50.3, 54.5, 121.9, 125.8, 126.4, 126.8, 127.4, 127.6, 128.6, 128.8, 129.1, 129.3, 132.6, 135.7, 136.6, 136.7, 142.2, 142.4, 148.6.

IR ν (neat, cm$^{-1}$): 3280, 3106, 2960, 2868, 1465, 1429, 1314.

MS (ESI) m/z: 514 (M+H)$^+$.

Anal. Calcd. for C$_{26}$H$_{31}$N$_3$O$_2$S$_3$: C, 60.79; H, 6.08; N, 8.18. Found: C, 60.58; H, 6.10; N, 8.34.

(b) N-Butyloxycarbonyl-3-[3-(2-thiophen-2-yl-imidazol-1-ylmethyl)phenyl]-5-iso-butylthiophene-2-sulfonamide To a solution of 3-[3-(2-thiophen-2-yl-imidazol-1-ylmethyl)phenyl]-5-iso-butyl-N-tert-butylthiophene-2-sulfonamide (42 mg, 0.082 mmol; see step (a)) in CH$_2$Cl$_2$ (1 mL) was added BCl$_3$ (0.3 mL, 1.0 M in hexane) and the reaction mixture was stirred for 1 h at ambient temperature. The reaction mixture was concentrated in vacuo. Water (5 mL) was added to the residue and this was then extracted with EtOAc. The combined organic phase was washed with water and brine, dried (over anhydrous MgSO$_4$) and concentrated in vacuo. To the crude product dissolved in CH$_2$Cl$_2$ (5 mL) was added Na$_2$CO$_3$ (39.0 mg, 0.377 mmol), water (2 mL) and butyl chloroformate (15.6 µL, 0.0123 mmol), and the reaction mixture was stirred for 9 h at ambient temperature. The reaction mixture was diluted with CH$_2$Cl$_2$ (30 mL) and washed with citric acid (10% aq), brine and water, dried (over anhydrous MgSO$_4$), concentrated in vacuo, and the residue purified by LCMS (20-100% CH$_3$CN in water) to give the title compound as a white solid in 55% yield, over two steps, (25 mg, 0.045 mmol).

$^1$H NMR δ (CDCl$_3$): 0.86 (t, J=7.2 Hz, 3H), 0.98 (d, J=6.6 Hz, 6H), 1.15-1.30 (m, 2H), 1.40-1.55 (m, 2H), 1.85-2.05 (m, 1H), 2.69 (d, J=6.9 Hz, 2H), 4.01 (t, J=6.6 Hz, 2H), 5.32 (s, 2H), 5.57 (br s, 1H), 6.71 (s, 1H), 6.96 (br s, 1H), 7.02 (dd, J=5.1, 3.6 Hz, 1H), 7.04-7.11 (m, 2H), 7.13 (dd, J=3.6, 0.8 Hz, 1H), 7.25 (s, 1H), 7.28-7.42 (m, 3H).

$^{13}$C NMR δ (CDCl$_3$): 13.6, 18.7, 22.2, 30.4, 30.5, 39.3, 50.2, 66.7, 121.8, 126.5, 126.7, 127.0, 127.4, 127.6, 128.5, 128.9, 129.2, 131.3, 131.9, 134.9, 136.4, 142.1, 145.5, 150.5, 151.5.

IR ν (neat, cm$^{-1}$): 3113, 3060, 2959, 2871, 1740, 1608, 1465, 1429, 1344, 1285, 1156.

MS (ESI) m/z: 558 (M+H)$^+$.

Anal. Calcd. for C$_{27}$H$_{31}$N$_3$O$_4$S$_3$: C, 58.14; H, 5.60; N, 7.53. Found: C, 57.97; H, 5.74; N, 7.59.

EXAMPLE 16

N-Butyloxycarbonyl-3-[3-(2-imidazol-1-yl-acetyl)-phenyl]-5-iso-butylthiophene-2-sulfonamide (a) 1-(3-Bromophenyl)-2-imidazol-1-ylethanone To a solution of 2-bromo-1-(3-bromophenyl)ethanone (120 mg, 0.432 mmol) in dioxane (2 mL) was added imidazole (58.8 mg, 0.864 mmol) and the reaction mixture was stirred for 1 h at 80° C. The reaction mixture was concentrated in vacuo and the residue was purified by flash chromatography using MeOH:CH$_2$Cl$_2$ (6:94) as eluent to give the sub-title compound in 68% yield (77.9 mg, 0.293 mmol).

$^1$H NMR δ (CDCl$_3$): 5.36 (s, 2H), 6.91 (s, 1H), 7.10 (s, 1H), 7.40 (apparent t, J=7.9 Hz, 1H), 7.47 (s, 1H), 7.76 (d, J=7.9 Hz, 1H), 7.87 (d, J=7.9 Hz, 1H), 8.07 (s, 1H).

$^{13}$C NMR δ (CDCl$_3$): δ2.4, 120.2, 123.3, 126.4, 129.5, 130.6, 130.9, 135.7, 137.1, 138.0, 190.5.

IR ν (neat, cm$^{-1}$): 3151, 3115, 3082, 2970, 1707, 1565, 1515, 1415.

MS (ESI) m/z: 265 ((M+H)$^+$, 100%), 267.0 ((M+H)$^+$+2, 100%).

Anal. Calcd. for C$_{11}$H$_9$BrN$_2$O: C, 49.84; H, 3.42; N, 10.57. Found: C, 49.53; H, 3.59; N, 10.40.

(b) 3-[3-(2-Imidazol-1-ylacetyl)phenyl]-5-iso-butyl-N-tert-butylthiophene-2-sulfonamide To a solution of 1-(3-bromophenyl)-2-imidazol-1-ylethanone (102 mg, 0.385 mmol; see step (a)) in toluene (10 mL) and ethanol (1 mL) was added 5-isobutyl-2-(N-tert-butylaminosulfonyl)thiophene-3-boronic acid (209 mg, 0.654 mmol; see Example 1(c)), Pd(PPh$_3$)$_4$ (26.7 mg, 0.023 mmol) and Na$_2$CO$_3$ (769 µL, 1.54 mmol, 2.0 M aq), and the reaction mixture was stirred for 4 h at 80° C. The reaction mixture was diluted with water (10 mL) and extracted with EtOAc. The combined organic phase was dried (over anhydrous MgSO$_4$), concentrated in vacuo, and the residue was purified by flash chromatography using MeOH:CH$_2$Cl$_2$ (6:94) as eluent to give the sub-title compound as a colourless syrup in 95% yield (168 mg, 0.366 mmol).

$^1$H NMR δ (CDCl$_3$): 0.98 (d, J=6.8 Hz, 6H), 1.05 (s, 9H), 1.82-2.02 (m, 1H), 2.70 (d, J=7.1 Hz, 2H), 5.04 (br s, 1H), 5.40 (s, 2H), 6.79 (s, 1H), 6.91 (d, J=1.2 Hz, 1H), 7.06 (br s, 1H), 7.43 (br s, 1H), 7.58 (apparent t, J=7.7 Hz, 1H), 7.80 (apparent d, J=7.7 Hz, 1H), 8.00 (apparent d, J=7.7 Hz, 1H), 8.33 (s, 1H).

$^{13}$C NMR δ (CDCl$_3$): 22.1, 29.6, 30.5, 39.1, 52.5, 54.8, 120.3, 127.6, 128.8, 129.1, 129.3, 134.0, 134.3, 135.7, 137.3, 138.1, 141.8, 149.0, 191.7.

IR ν (neat, cm$^{-1}$): 3272, 3073, 2959, 2869, 1701, 1603, 1580, 1510, 1428, 1304.

MS (ESI) m/z: 460 (M+H)$^+$.

Anal. Calcd. for C$_{23}$H$_{29}$N$_3$O$_3$S$_2$: C, 60.10; H, 6.36; N, 9.14. Found: C, 59.78; H, 6.28; N, 9.02.

(c) N-Butyloxycarbonyl-3-[3-(2-imidazol-1-ylacetyl) phenyl]-5-iso-butylthio-phene-2-sulfonamide To a solution of 3-[3-(2-imidazol-1-ylacetyl)phenyl]-5-iso-butyl-N-tert-butylthiophene-2-sulfonamide (50.5 mg, 0.110 mmol; see step (b)) in $CH_2Cl_2$ (1 mL) was added $BCl_3$ (0.22 mL, 1.0 M in hexane) and the reaction mixture was stirred for 1 h at ambient temperature. The reaction mixture was concentrated in vacuo. $CH_2Cl_2$ (30 mL) was added to the residue and this was washed with water. The organic phase was dried (over anhydrous $MgSO_4$) and concentrated in vacuo. To the crude product dissolved in $CH_2Cl_2$ (5 mL) was added $Na_2CO_3$ (52.4 mg, 0.495 mmol), water (2 mL) and butyl chloroformate (34.3 µL, 0.270 mmol), and the reaction mixture was stirred for 2 h at ambient temperature. The reaction mixture was diluted with $CH_2Cl_2$ (30 mL) and washed with citric acid (10% aq), brine and water, dried (over anhydrous $MgSO_4$), concentrated in vacuo, and the residue purified by LCMS (20-100% $CH_3CN$ in water) to give the title compound as a white solid in 32% yield, over two steps, (18 mg, 0.036 mmol).

$^1H$ NMR $\delta$ ($CDCl_3$): 0.85 (t, J=7.3 Hz, 3H), 0.98 (d, J=6.6 Hz, 6H), 1.15-1.32 (m, 2H), 1.35-1.55 (m, 2H), 1.82-2.00 (m, 1H), 2.67 (d, J=6.9 Hz, 2H), 3.94 (t, J=6.6 Hz, 2H), 5.40 (s, 2H), 6.70 (s, 1H), 6.82 (s, 1H), 6.93 (s, 1H), 7.42 (apparent t, J=7.7, 7.7 Hz, 1H), 7.60 (d, J=7.7 Hz, 1H), 7.73 (s, 1H), 7.85 (d, J=7.7 Hz, 1H), 8.29 (s, 1H), 9.71 (br s, 1H).

$^{13}C$ NMR $\delta$ ($CDCl_3$): 13.7, 18.9, 22.3, 30.5, 30.8, 39.2, 53.2, 65.4, 121.2, 124.2, 127.5, 128.5, 128.7, 129.6, 133.3, 134.4, 135.6, 135.7, 137.1, 142.0, 149.3, 154.5, 191.0.

IR $\nu$ (neat, $cm^{-1}$): 3140, 3064, 2957, 2870, 1701, 1662, 1581, 1464, 1261.

MS (ESI) m/z: 504 $(M+H)^+$.

Anal. Calcd. for $C_{24}H_{29}N_3O_5S_2$: C, 57.24; H, 5.80; N, 8.34. Found: C, 57.05; H, 5.98; N, 8.28.

EXAMPLE 17

N-Butyloxycarbonyl-3-{3-[2-(2-ethylimidazol-1-yl)acetyl]phenyl}-5-iso-butyl-thiophene-2-sulfonamide (a) 1-(3-Bromophenyl)-2-(2-ethylimidazol-1-yl)ethanone To a solution of 2-bromo-1-(3-bromophenyl)ethanone (120 mg, 0.432 mmol) in dioxane (2 mL) was added 2-ethylimidazole (83.0 mg, 0.864 mmol) and the reaction mixture was stirred for 1 h at 80° C. The reaction mixture was concentrated in vacuo and the residue was purified by flash chromatography using $MeOH:CH_2Cl_2$ (6:94) as eluent to give the sub-title compound in 51% yield (65 mg, 0.22 mmol).

$^1H$ NMR $\delta$ ($CDCl_3$): 1.28 (t, J=7.5 Hz, 3H), 2.52 (q, J=7.5 Hz, 2H), 5.27 (s, 2H), 6.77 (s, 1H), 6.99 (s, 1H), 7.40 (apparent t, J=7.9 Hz, 1H), 7.76 (d, J=7.9 Hz, 1H), 7.87 (d, J=7.9 Hz, 1H), 8.07 (s, 1H).

$^{13}C$ NMR $\delta$ ($CDCl_3$): 11.7, 19.8, 51.6, 120.2, 123.3, 126.3, 127.5, 130.6, 130.9, 135.8, 137.1, 149.8, 190.6.

IR $\nu$ (neat, $cm^{-1}$): 3126, 3096, 3064, 2965, 1700, 1588, 1568, 1496, 1419.

MS (ESI) m/z: 293 ($(M+H)^+$, 100), 295 ($(M+H)^+$+2, 100).

Anal. Calcd. for $C_{13}H_{13}BrN_2O$: C, 53.26; H, 4.47; N, 9.56. Found: C, 53.18; H, 4.49; N, 9.55.

(b) 3-{3-[2-(2-Ethylimidazol-1-yl)acetyl]phenyl}-5-iso-butyl-N-tert-butylthio-phene-2-sulfonamide To a solution of 1-(3-bromophenyl)-2-(2-ethylimidazol-1-yl)ethanone (54.6 mg, 0.186 mmol; see step (a)) in toluene (10 mL) and ethanol (1 mL) was added 5-isobutyl-2-(N-tert-butylaminosulfonyl)thiophene-3-boronic acid (101 mg, 0.317 mmol; see Example 1(c)), $Pd(PPh_3)_4$ (12.9 mg, 0.0112 mmol), $Na_2CO_3$ (373 µL, 0.745 mmol, 2.0 M aq) and the reaction mixture was stirred for 4 h at 80° C. The reaction mixture was diluted with water (10 mL) and extracted with EtOAc. The combined organic phase was dried (over anhydrous $MgSO_4$), concentrated in vacuo, and the residue purified by flash chromatography using $MeOH:CH_2Cl_2$ (5:95) as eluent to give the sub-title compound as a colourless syrup in 94% yield (85.5 mg, 0.175 mmol).

$^1H$ NMR $\delta$ ($CDCl_3$): 0.99 (d, J=6.6 Hz, 6H), 1.08 (s, 9H), 1.31 (t, J=7.4 Hz, 3H), 1.83-2.00 (m, 1H), 2.57 (q, J=7.4 Hz, 2H), 2.71 (d, J=7.1 Hz, 2H), 4.21 (s, 1H), 5.34 (s, 2H), 6.79 (s, 1H), 6.82 (d, J=1.1 Hz, 1H), 7.01 (d, J=1.1 Hz, 1H), 7.61 (apparent t, J=7.7, 7.7 Hz, 1H), 7.84 (apparent dt, J=7.7, 1.3 Hz, 1H), 8.01 (apparent dt, J=7.7, 1.3 Hz, 1H), 8.30 (apparent t, J=1.3 Hz, 1H).

$^{13}C$ NMR $\delta$ ($CDCl_3$): 11.8, 19.9, 22.1, 29.6, 30.5, 39.1, 51.7, 54.9, 120.3, 127.3, 127.6, 128.8, 129.08, 129.13, 134.1, 134.4, 135.7, 137.1, 141.9, 149.0, 149.8, 191.8.

IR $\nu$ (neat, $cm^{-1}$): 3272, 3074, 2964, 2872, 1702, 1579, 1497, 1311.

MS (ESI) m/z: 488 $(M+H)^+$.

Anal. Calcd. for $C_{25}H_{33}N_3O_3S_2$: C, 61.57; H, 6.82; N, 8.62. Found: C, 61.27; H, 6.67; N, 8.44.

(c) N-Butyloxycarbonyl-3-{3-[2-(2-ethylimidazol-1-yl)acetyl]phenyl}-5-iso-butyl-thiophene-2-sulfonamide To a solution of 3-{3-[2-(2-ethylimidazol-1-yl)acetyl]phenyl}-5-iso-butyl-N-tert-butylthiophene-2-sulfonamide (74.5 mg, 0.153 mmol; see step (b)) in TFA (3 mL) was added anisole (150 µL) and the reaction mixture was stirred for 28 h at ambient temperature. The reaction mixture was concentrated in vacuo and dried in vacuo overnight. To the crude product dissolved in $CH_2Cl_2$ (7 mL) was added $Na_2CO_3$ (72.9 mg, 0.688 mmol), water (2 mL) and butyl chloroformate (33.0 µL, 0.260 mmol), and the reaction mixture was stirred overnight at ambient temperature. The reaction mixture was diluted with $CH_2Cl_2$ (30 mL) and washed with citric acid (10% aq), brine and water, dried (over anhydrous $MgSO_4$), concentrated in vacuo, and the residue purified by flash chromatography using $MeOH:CH_2Cl_2$ (8:92) as eluent to give the sub-title compound in 47% yield, over two steps, (38.5 mg, 0.0724 mmol).

$^1H$ NMR $\delta$ ($CDCl_3$): 0.80 (t, J=7.2 Hz, 3H), 0.94 (d, J=6.6 Hz, 6H), 1.05-1.30 (m, 5H), 1.30-1.50 (m, 2H), 1.75-1.95 (m, 1H), 2.50-2.90 (m, 4H), 3.87 (t, J=6.7 Hz, 2H), 5.67 (s, 2H), 6.73 (s, 1H), 7.01 (s, 1H), 7.09 (s, 1H), 7.38 (m, 1H), 7.76 (d, J=7.7 Hz, 1H), 7.91 (d, J=7.4 Hz, 1H), 8.63 (s, 1H), 10.57 (br s, 1H).

$^{13}C$ NMR $\delta$ ($CDCl_3$): 11.9, 13.7, 18.3, 19.0, 22.2, 30.4, 31.0, 39.1, 53.2, 64.8, 120.0, 122.2, 127.3, 128.1, 128.6, 130.4, 132.8, 134.8, 136.2, 138.7, 140.1, 147.0, 149.2, 158.7.

IR $\nu$ (neat, $cm^{-1}$): 3145, 2957, 2872, 1700, 1654, 1609, 1463, 1260.

MS (ESI) m/z: 532 $(M+H)^+$.

Anal. Calcd. for $C_{26}H_{33}N_3O_5S_2$: C, 58.73; H, 6.26; N, 7.90. Found: C, 58.50; H, 6.27; N, 7.74.

EXAMPLE 18

N-Butyloxycarbonyl-3-[3-(2-benzoimidazol-1-yl-acetyl)-phenyl]-5-iso-butylthio-phene-2-sulfonamide (a) 2-Benzoimidazol-1-yl-1-(3-bromophenyl)ethanone To a solution of 2-bromo-1-(3-bromophenyl)ethanone (120 mg, 0.432 mmol) in dioxane (2 mL) was added benzoimidazole (102.0 mg, 0.864 mmol) and the reaction mixture was stirred for 1 h at 80° C. The reaction mixture was concentrated in vacuo and the residue was purified by flash chromatography using MeOH:$CH_2Cl_2$ (4:96) as eluent to give the sub-title compound in 53% yield (71.8 mg, 0.227 mmol).

$^1$H NMR δ ($CDCl_3$): 5.38 (s, 2H), 7.02-7.12 (m, 1H), 7.12-7.26 (m, 2H), 7.33 (apparent t, J=7.9 Hz, 1H), 7.60-7.86 (m, 4H), 8.04 (m, 1H).

$^{13}$C NMR δ ($CDCl_3$): δ0.3, 109.2, 120.5, 122.4, 123.3, 123.4, 126.4, 130.7, 131.0, 134.0, 135.7, 137.2, 143.4, 143.6, 190.1.

IR ν (neat, $cm^{-1}$): 3090, 3056, 2926, 1708, 1615, 1566, 1501, 1417, 1351.

MS (ESI) m/z: 315 ((M+H)$^+$, 100), 317 ((M+H)$^+$+2, 100).

Anal. Calcd. for $C_{15}H_{11}BrN_2O$: C, 57.16; H, 3.52; N, 8.89. Found: C, 56.90; H, 3.56; N, 8.75.

(b) 3-[3-(2-Benzoimidazol-1-ylacetyl)phenyl]-5-iso-butyl-N-tert-butylthiophene-2-sulfonamide To a solution of 2-benzoimidazol-1-yl-1-(3-bromophenyl) ethanone (42.7 mg, 0.136 mmol; see step (a)) in toluene (7 mL) and ethanol (1 mL) was added 5-isobutyl-2-(N-tert-butylaminosulfonyl)thiophene-3-boronic acid (73.5 mg, 0.230 mmol; see Example 1(c)), Pd(PPh$_3$)$_4$ (9.4 mg, 8.1 µmol) and Na$_2$CO$_3$ (271 µL, 0.542 mmol, 2.0 M aq), and the reaction mixture was stirred for 3 h at 80° C. The reaction mixture was diluted with water (10 mL) and extracted with EtOAc. The combined organic phase was dried (over anhydrous MgSO$_4$), concentrated in vacuo, and the residue was purified by flash chromatography using MeOH:$CH_2Cl_2$ (5:95) as eluent to give the sub-title compound as a colourless syrup in 90% yield (62 mg, 0.122 mmol).

$^1$H NMR δ ($CDCl_3$): 0.99 (d, J=6.6 Hz, 6H), 1.08 (s, 9H), 1.86-2.02 (m, 1H), 2.71 (d, J=6.9 Hz, 2H), 4.22 (br s, 1H), 5.63 (s, 2H), 6.80 (s, 1H), 7.18-7.34 (m, 3H), 7.62 (apparent d, J=7.7 Hz, 1H), 7.76-7.90 (m, 2H), 7.97 (d, J=4.3 Hz, 1H), 8.05 (m, 1H), 8.39 (m, 1H).

$^{13}$C NMR δ ($CDCl_3$): 22.1, 29.7, 30.5, 39.1, 50.4, 54.8, 109.4, 120.3, 122.3, 123.2, 127.7, 128.8, 129.1, 129.3, 134.0, 134.1, 134.4, 135.7, 137.3, 141.9, 143.1, 143.9, 149.0, 191.4.

IR ν (neat, cm$^-$): 3277, 3065, 2961, 2869, 1702, 1616, 1580, 1498, 1461, 1312. MS (ESI) m/z: 510 (M+H)$^+$.

Anal. Calcd. for $C_{27}H_{31}N_3O_3S_2$: C, 63.63; H, 6.13; N, 8.24. Found: C, 63.42; H, 6.05; N, 8.22.

(c) N-Butyloxycarbonyl-3-[3-(2-benzoimidazol-1-ylacetyl)phenyl]-5-iso-butyl-thiophene-2-sulfonamide To a solution of 3-[3-(2-benzoimidazol-1-ylacetyl)phenyl]-5-iso-butyl-N-tert-butylthiophene-2-sulfonamide (54.4 mg, 0.107 mmol; see step (b)) in TFA (3 mL) was added anisole (150 µL) and the reaction mixture was stirred for 28 h at ambient temperature. The reaction mixture was concentrated in vacuo and dried in vacuo overnight. To the crude product dissolved in pyridine (1.5 mL) was added pyrrolidinopyridine (31.6 mg, 0.214 mmol) and butyl chloroformate (135.7 µL, 1.07 mmol), and the reaction mixture was stirred overnight. Another portion of pyrrolidinopyridine (31.6 mg, 0.214 mmol) and butyl chloroformate (135.7 µL, 1.07 mmol) was added and the reaction mixture was stirred overnight. Citric acid (10 mL, 10% aq) was added to the reaction mixture, which was then extracted with EtOAc, dried (over anhydrous MgSO$_4$), concentrated in vacuo, and the residue purified by flash chromatography using MeOH:$CH_2Cl_2$ (5:95) as eluent to give the title compound in 36% yield, over two steps, (21 mg, 0.038 mmol).

$^1$H NMR δ ($CDCl_3$): 0.84 (t, J=7.3 Hz, 3H), 1.01 (d, J=6.6 Hz, 6H), 1.14-1.34 (m, 2H), 1.42-1.60 (m, 2H), 1.86-2.02 (m, 1H), 2.72 (d, J=6.9 Hz, 2H), 4.07 (t, J=6.4 Hz, 2H), 6.78 (s, 1H), 7.04-7.30 (m, 3H), 7.37 (apparent t, J=7.7 Hz, 1H), 7.45 (d, J=7.7 Hz, 1H), 7.52-7.70 (m, 2H), 7.81 (s, 1H), 8.33 (s, 1H), 8.89 (br s, 1H).

$^{13}$C NMR δ ($CDCl_3$): 13.6, 18.8, 22.3, 30.5, 30.6, 39.3, 49.9, 66.1, 109.7, 119.6, 122.8, 123.7, 127.6, 128.9, 129.5, 133.4, 133.6, 133.9, 134.2, 135.3, 140.4, 143.4, 143.8, 150.7, 152.5, 190.7.

IR ν (neat, cm$^{-1}$): 2500-3500 (br), 3061, 2959, 2871, 1739, 1702, 1604, 1580, 1499, 1462, 1343, 1289.

MS (ESI) m/z: 554 (M+H)$^+$.

Anal. Calcd. for $C_{28}H_{31}N_3O_5S_2$: C, 60.74; H, 5.64; N, 7.59. Found: C, 60.51; H, 5.64; N, 7.55.

EXAMPLE 19

N-Butyloxycarbonyl-3-[3-(2-benzoimidazol-1-yl-acetyl)-phenyl]-5-iso-butylthio-phene-2-sulfonamide (a) 1-[2-(3-Bromophenyl)ethyl]-1H-imidazole To a solution of 1-(3-Bromophenyl)-2-imidazol-1-ylethanone (100 mg, 0.377 mmol; see Example 16(a)) in MeOH (5 mL) was added NaBH$_4$ (14.2 mg, 0.377 mmol) and the reaction mixture was stirred for 30 min. The reaction mixture was concentrated in vacuo, after which water (3 mL) and CH$_2$Cl$_2$ (10 mL) were added. The solution was neutralised with HCl (2M aq) and extracted with CH$_2$Cl$_2$. The combined organic phase was dried (over anhydrous MgSO$_4$) and concentrated in vacuo to give the corresponding alcohol in 86% yield (86.2 mg, 0.323 mmol). The crude alcohol (55.4 mg, 0.207 mmol) was dissolved in THF (10 mL), NaH (55%, 10.0 mg, 0.415 mmol, washed twice with hexane) was added and the mixture was stirred for 2 h at ambient temperature. CS$_2$ (80.9 mg, 1.04 mmol) was added and the reaction mixture become clear after 15 min, after which MeI (147.2 mg, 1.04 mmol) was added. After 30 min the reaction mixture was poured into water and extracted with EtOAc. The combined organic phase was dried (over anhydrous MgSO$_4$), concentrated in vacuo, and the residue purified by flash chromatography using MeOH:CH$_2$Cl$_2$ (4:96) as eluent to give the thioester as a colourless syrup in 99% yield (73.4 mg, 0.205 mmol). To the thioester (73.4 mg, 0.205 mmol) dissolved in THF (10 mL) was added Bu$_3$SnH (59.8 mg, 0.205 mmol) and AIBN (2 mg, 0.012 mmol). The reaction mixture was refluxed for 3 h and then a second portion of Bu$_3$SnH (11.2 mg, 0.0385 mmol) and AIBN (1 mg, 0.006 mmol) was added and the reaction was refluxed for an additional 40 min. The solvent was removed in vacuo and the residue dissolved in CH$_3$CN (20 mL) and extracted with hexane. The solvent was removed in vacuo and the residue was purified by flash chromatography using MeOH:CH$_2$Cl$_2$ (6:94) as eluent to give the sub-title compound as a colourless syrup in 74% yield (38.2 mg, 0.152 mmol).

$^1$H NMR δ (CDCl$_3$): 3.00 (t, J=7.1 Hz, 2H), 4.15 (t, J=7.1 Hz, 2H), 6.84 (br s, 1H), 6.92 (d, J=7.7 Hz, 1H), 7.04 (br s, 1H), 7.13 (apparent t, J=7.7 Hz, 1H), 7.20-7.28 (m, 1H), 7.33 (br s, 1H), 7.36 (d, J=7.7 Hz, 1H).

$^{13}$C NMR δ (CDCl$_3$): 37.4, 48.1, 118.7, 122.7, 127.2, 129.7, 130.1, 130.3, 131.5, 137.1, 139.6.

IR ν (neat, cm$^{-1}$): 3109, 3059, 2934, 1596, 1567, 1506, 1475.

MS (ESI) m/z: 253 ((M+H)$^+$+2, 100%), 251 ((M+H)$^+$, 100%).

Anal. Calcd. for C$_{11}$HI BrN$_2$.×⅛H$_2$O C, 52.1; H, 4.5; N, 11.1. Found: C, 51.7; H, 4.6; N, 11.5.

(b) 3-[3-(2-Benzoimidazol-1-ylacetyl)phenyl]-5-isobutyl-N-tert-butylthiophene-2-sulfonamide To a solution of 1-[2-(3-bromophenyl)ethyl]-1H-imidazole (51.5 mg, 0.205 mmol; see step (a)) in toluene (10 mL) and ethanol (1 mL) was added 5-isobutyl-2-(N-tert-butylaminosulfonyl)thiophene-3-boronic acid (111.3 mg, 0.349 mmol; see Example 1(c)), Pd(PPh$_3$)$_4$ (14.2 mg, 23.4 μmol) and Na$_2$CO$_3$ (410 μL, 0.820 mmol, 2.0 M aq), and the reaction mixture was stirred for 4 h at 90° C. The reaction mixture was diluted with water (10 mL) and extracted with EtOAc. The combined organic phase was dried (over anhydrous MgSO$_4$), concentrated in vacuo, and the residue was purified by flash chromatography using EtOAc:hexane (3:7) as eluent to give the sub-title compound in 91% yield (83.3 mg, 0.187 mmol).

$^1$H NMR δ (CDCl$_3$): 0.96 (d, J=7.1 Hz, 6H), 0.98 (s, 9H), 1.82-2.00 (m, 1H), 2.66 (d, J=7.1 Hz, 2H), 3.08 (t, J=6.8 Hz, 2H), 4.22 (t, J=6.8 Hz, 2H), 4.32 (br s, 1H), 6.69 (s, 1H), 6.89 (s, 1H), 7.00 (s, 1H), 7.08 (d, J=7.4 Hz, 1H), 7.20-7.43 (m, 4H).

$^{13}$C NMR δ (CDCl$_3$): 22.1, 29.4, 30.4, 37.2, 39.1, 48.0, 54.4, 118.7, 127.3, 128.5, 128.7, 129.0, 129.4, 129.6, 135.3, 136.4, 137.2, 137.5, 142.9, 148.3.

IR ν (neat, cm$^{-1}$): 3285, 3066, 2959, 2870, 1606, 1510, 1463, 1390, 1311.

MS (ESI) m/z: 446 (M+H)$^+$.

Anal. Calcd. for C$_{23}$H$_{31}$N$_3$O$_2$S$_2$: C, 61.99; H, 7.01; N, 9.43. Found: C, 61.85; H, 6.93; N, 9.47.

(c) N-Butyloxycarbonyl-3-[3-(2-benzoimidazol-1-ylacetyl)phenyl]-5-iso-butyl-thiophene-2-sulfonamide To a solution of 3-[3-(2-Benzoimidazol-1-ylacetyl)phenyl]-5-iso-butyl-N-tert-butylthiophene-2-sulfonamide (67.3 mg, 0.151 mmol; see step (b)) in CH$_2$Cl$_2$ (1 mL) was added BCl$_3$ (0.3 mL, 1.0 M in hexane) and the reaction mixture was stirred for 1 h at ambient temperature. The reaction mixture was concentrated in vacuo. CH$_2$Cl$_2$ (30 mL) was added to the residue and this was washed with water. The organic phase was dried (over anhydrous MgSO$_4$), concentrated in vacuo. To the crude product dissolved in CH$_2$Cl$_2$ (5 mL) was added Na$_2$CO$_3$ (72 mg, 0.680 mmol), water (2 mL) and butyl chloroformate (24.9 μL, 0.196 mmol), and the reaction mixture was stirred for 2 h at ambient temperature. The reaction mixture was diluted with CH$_2$Cl$_2$ (30 mL) and washed with citric acid (10% aq), brine and water, dried (over anhydrous MgSO$_4$), concentrated in vacuo, and the residue purified by flash chromatography using MeOH:CH$_2$Cl$_2$ (6:94) as eluent to give the title compound in 90% yield, over two steps, (66.2 mg, 0.135 mmol).

$^1$H NMR δ (CDCl$_3$): 0.90 (t, J=7.2 Hz, 3H), 0.97 (d, J=6.6 Hz, 6H), 1.22-1.40 (m, 2H), 1.50-1.64 (m, 2H), 1.84-2.00 (m, 1H), 2.66 (d, J=7.1 Hz, 2H), 2.87 (t, J=6.4 Hz, 2H), 4.06 (t, J=6.6 Hz, 2H), 4.18 (t, J=6.4 Hz, 2H), 6.61 (s, 1H), 6.89 (s, 1H), 6.91-7.08 (m, 3H), 7.16-7.34 (m, 3H), 8.80 (br s, 1H).

$^{13}$C NMR δ (CDCl$_3$): 13.7, 18.9, 22.3, 30.4, 30.7, 37.5, 39.2, 49.1, 65.8, 119.0, 126.8, 127.96, 128.0, 128.4, 128.8, 129.4, 133.6, 135.6, 136.6, 137.4, 144.4, 149.6, 153.2.

IR ν (neat, cm$^{-1}$): 3138, 3045, 2956, 2862, 1650, 1579, 1487, 1454, 1293.

MS (ESI) m/z: 490 (M+H)$^+$.

Anal. Calcd. for C$_{24}$H$_{31}$N$_3$O$_4$S$_2$: C, 58.87; H, 6.38; N, 8.58. Found: C, 58.71; H, 6.52; N, 8.57.

EXAMPLE 20

Title compounds of the Examples were tested in Tests A and B above and were found to exhibit an affinity for AT2 receptors of less than Ki=100 nM (e.g. less than 50 nM) and an affinity to AT1 receptors of more than Ki=500 nM (e.g. more than 1 μM).

EXAMPLE 21

Title compounds of the Examples were tested in Test C above and were found to stimulate markedly mucosal alkalisation. This effect was blocked by co-administration of the selective AT2 receptor antagonist PD123319 (Sigma Chemical Company).

The invention claimed is:
1. A compound of formula I,

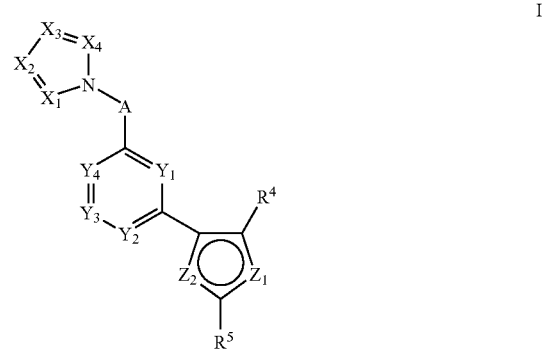

wherein
A represents —CH$_2$—, —C(O)—, —C(O)—CH$_2$— or —CH$_2$—CH$_2$—;
one of X$_1$ and X$_2$ represents —N— and the other represents —C(R$^1$)—;
X$_3$ represents —N— or —C(R$^2$)—;
X$_4$ represents —N— or —C(R$^3$)—;
R$^1$, R$^2$ and R$^3$ independently represent H, C$_{1-6}$ alkyl, C$_{1-6}$ alkoxy, C$_{1-6}$ alkoxy-C$_{1-6}$-alkyl, Ar$^1$, Het$^1$, C$_{1-3}$ alkyl-Ar$^2$, C$_{1-3}$ alkyl-Het$^2$, C$_{1-3}$ alkoxy-Ar$^3$, C$_{1-3}$ alkoxy-Het$^3$, halo, —C(O)—C$_{1-6}$ alkyl, —C(O)—Ar$^4$ or —C(O)—Het$^4$; or
R$^2$ and R$^3$ may be linked to form, along with the carbon atoms to which they are attached, a 5- or 6-membered aromatic ring optionally containing one to three heteroatoms;
Ar$^1$, Ar$^2$, Ar$^3$ and Ar$^4$ each independently represent a C$_{6-10}$ aryl group, which group is optionally substituted by one or more substituents selected from =O, —OH, cyano, halo, nitro, $C_{1-6}$ alkyl (optionally terminated by —N(H)C(O)OR$^{11a}$), $C_{1-6}$ alkoxy, phenyl, —N(R$^{12a}$)R$^{12b}$, —C(O)R$^{12c}$, —C(O)OR$^{12d}$, —C(O)N(R$^{12e}$)R$^{12f}$, —N(R$^{12g}$)C(O)R$^{12h}$, —N(R$^{12i}$)C(O)N(R$^{12j}$)R$^{12k}$, —N(R$^{12m}$)S(O)$_2$R$^{11b}$, —S(O)$_n$R$^{11c}$, —OS(O)$_2$R$^{11d}$; and —S(O)$_2$N(R$^{12n}$)R$^{12p}$;

Het$^1$, Het$^2$, Het$^3$ and Het$^4$ each independently represent a four- to twelve-membered heterocyclic group containing one or more heteroatoms selected from oxygen, nitrogen and/or sulfur, which heterocyclic group is optionally substituted by one or more substituents selected from =O, —OH, cyano, halo, nitro, $C_{1-6}$ alkyl (optionally terminated by —N(H)C(O)OR$^{11a}$), $C_{1-6}$ alkoxy, phenyl, —N(R$^{12a}$)R$^{12b}$, —C(O)R$^{12c}$, —C(O)OR$^{12d}$, —C(O)N(R$^{12e}$)R$^{12f}$, —N(R$^{12g}$)C(O)R$^{12h}$, —N(R$^{12i}$)C(O)N(R$^{12j}$)R$^{12k}$, —N(R$^{12m}$)S(O)$_2$R$^{11b}$, —S(O)$_n$R$^{11c}$, —OS(O)$_2$R$^{11d}$; and —S(O)$_2$N(R$^{12n}$)R$^{12p}$;

R$^{11a}$ to R$^{11d}$ independently represent $C_{1-6}$ alkyl;

R$^{12a}$ to R$^{12p}$ independently represent H or $C_{1-6}$ alkyl;

n represents 0, 1 or 2;

$Y_1$, $Y_2$, $Y_3$ and $Y_4$ independently represent —CH— or —CF—;

$Z_1$ represents —CH—, —O—, —S—, —N— or —CH=CH—;

$Z_2$ represents —CH—, —O—, —S— or —N—;

provided that:

(a) $Z_1$ and $Z_2$ are not the same;

(b) when $Z_1$ represents —CH=CH—, then $Z_2$ may only represent —CH— or —N—; and (c) other than in the specific case in which $Z_1$ represents —CH=CH—, and $Z_2$ represents —CH—, when one $Z_1$ and $Z_2$ represents —CH—, then the other represents —O— or —S—;

R$^4$ represents —S(O)$_2$N(H)C(O)R$^6$, —S(O)$_2$N(H)S(O)$_2$R$^6$, —C(O)N(H)S(O)$_2$R$^6$, or, when $Z_1$ represents —CH=CH—, R$^4$ may represent —N(H)S(O)$_2$N(H)C(O)R$^7$ or —N(H)C(O)N(H)S(O)$_2$R$^7$;

R$^5$ represents $C_{1-6}$ alkyl, $C_{1-6}$ alkoxy, $C_{1-6}$ alkoxy-$C_{1-6}$-alkyl or di-$C_{1-3}$-alkylamino-$C_{1-4}$-alkyl;

R$^6$ represents $C_{1-6}$ alkyl, $C_{1-6}$ alkoxy, $C_{1-6}$ alkoxy-$C_{1-6}$-alkyl, $C_{1-3}$ alkoxy-$C_{1-6}$-alkoxy, $C_{1-6}$ alkylamino or di-$C_{1-6}$ alkylamino; and R$^7$ represents $C_{1-6}$ alkyl, or a pharmaceutically-acceptable salt thereof.

2. A compound as claimed in claim 1, wherein A represents —CH$_2$—, —C(O)—CH$_2$— or —CH$_2$—CH$_2$—.

3. A compound as claimed in claim 1, wherein X$^3$ represents —C(R$^2$)—.

4. A compound as claimed in claim 1, wherein X$^4$ represents —C(R$^3$)—.

5. A compound as claimed in claim 1, wherein R$^1$ represents hydrogen, halo, $C_{1-4}$ alkyl (optionally substituted by one or more fluoro atoms), Ar$^1$, Het$^1$ or —C(O)—$C_{1-3}$ alkyl.

6. A compound as claimed in claim 1, wherein R$^2$ represents H.

7. A compound as claimed in claim 1, wherein R$^3$ represents H.

8. A compound as claimed in claim 1, wherein R$^2$ and R$^3$ are linked to form a further benzene ring, optionally containing one or two heteroatoms.

9. A compound as claimed in claim 8, wherein R$^2$ and R$^3$ are linked to form a further benzene or pyridine ring.

10. A compound as claimed in claim 1, wherein $Y_1$, $Y_2$, $Y_3$ and $Y_4$ all represent —CH—.

11. A compound as claimed in claim 1, wherein $Z_1$ represents —S— or —CH=CH—.

12. A compound as claimed in claim 11, wherein $Z_1$ represents —S—.

13. A compound as claimed in claim 1, wherein $Z_2$ represents —CH—.

14. A compound as claimed in claim 1, wherein R$^5$ represents $C_{1-4}$ alkyl.

15. A compound as claimed in claim 14, wherein R$^5$ represents iso-butyl.

16. A compound as claimed in claim 1, wherein, when R$^4$ represents —S(O)$_2$N(H)C(O)R$^6$, —S(O)$_2$N(H)S(O)$_2$R$^6$ or —C(O)N(H)S(O)$_2$R$^6$, R$^6$ represents n-butoxymethyl, iso-butoxy or n-butoxy.

17. A compound as claimed in claim 1, wherein R$^4$ represents —S(O)$_2$N(H)C(O)R$^6$.

18. A compound as claimed in claim 17, wherein R$^6$ represents n-butoxymethyl, iso-butoxy or n-butoxy.

19. A compound as claimed in claim 16, wherein R$^6$ represents n-butoxy.

20. A pharmaceutical formulation including a compound as defined in claim 1, or a pharmaceutically acceptable salt thereof, in admixture with a pharmaceutically acceptable adjuvant, diluent or carrier.

* * * * *